(12) United States Patent
Watanabe et al.

(10) Patent No.: US 9,868,765 B2
(45) Date of Patent: Jan. 16, 2018

(54) T CELL RECEPTOR AND USES THEREOF

(71) Applicant: MEDICAL & BIOLOGICAL LABORATORIES CO., LTD., Nagoya-shi, Aichi (JP)

(72) Inventors: Kazue Watanabe, Ina (JP); Shingo Toji, Ina (JP)

(73) Assignee: MEDICAL & BIOLOGICAL LABORATORIES CO., LTD., Nagoya-shi, Aichi (JP)

(*) Notice: Subject to any disclaimer, the term of this patent is extended or adjusted under 35 U.S.C. 154(b) by 966 days.

(21) Appl. No.: 14/012,604

(22) Filed: Aug. 28, 2013

(65) Prior Publication Data
US 2014/0212888 A1 Jul. 31, 2014

(30) Foreign Application Priority Data

Jan. 30, 2013 (JP) ................................ 2013-015844

(51) Int. Cl.
| | | |
|---|---|---|
| C07H 21/04 | (2006.01) |
| C07K 7/08 | (2006.01) |
| C07K 16/28 | (2006.01) |
| C07K 14/725 | (2006.01) |
| C07K 14/47 | (2006.01) |

(52) U.S. Cl.
CPC ............ *C07K 7/08* (2013.01); *C07K 14/4748* (2013.01); *C07K 14/7051* (2013.01); *C07K 16/2803* (2013.01)

(58) Field of Classification Search
None
See application file for complete search history.

(56) References Cited

PUBLICATIONS

Janeway, Immunobiology, 2001, pp. 138-139.*
Janeway et al., Immunobiology, 5th Ed., Garland Science, pp. 106-108 and 260-263, (2001).*
Garcia et al., Cell, vol. 122, 333-336, Aug. 12, 2005.*
Portolano et al., J Immunol. Feb. 1, 1993;150(3):880-7.*
Altman et al., "Phenotypic Analysis of Antigen-Specific T Lymphocytes", Science, 274:94-96 (1996).
Sapporo et al, "The 71st Annual Meeting of the Japanese Cancer Association", Proceedings, Sapporo Medical University, Sep. 19-21, 2012.
Morgan et al., "Cancer Regression in Patients after Transfer of Genetically Engineered Lymphocyes", Science 314:126-129 (2006).
Van Der Bruggen, "A Gene Encoding an Antigen Recognized by Cytolytic T Lymphocytes on a Human Malenoma", Science, 254:1643-1647 (1991).
Cox et al., "Identification of a Peptide Recognized by Five Melanoma-Specific Human Cytotoxic T Cell Lines", Science, 264:716-719 (1994).
Murphy et al., "A novel MHC class II epitope expressed in thymic medulla but not cortex", Nature, 338:765-768 (1989).
Rosenberg et al., "Immunologic and therapeutic evaluation of a synthetic peptide vaccine for the treatment of patients with metastatic melanoma", Nat. Med., 4(3):321-327 (1998).
Wülfing et al., "Correctly Folded T-cell Receptor Fragments in the Periplasm of *Escherichia coli*", J. Mol. Biol., 242:655-669 (1994).
Porgador et al., "Localization, Quantitation, and In Situ detection of specific peptide-MHC Class I complexes using a monoclonal antibody", Immunity, 6:715-726 (1997).
Subbramanian et al., "Engineered T-cell receptor tetramers bind MHC-peptide complexes with high affinity", Nature Biotechnology, 22(11):1429-1434 (2004).
Itoh et al., "High-throughput DNA typing of HLA-A, -B, -C and -DRB1 loci by a PCR-SSOP-Luminex method in the Japanese population", Immunogenetics, 57:717-729 (2005).
Cheever et al., "The prioritization of Cancer Antigens: A National Cancer Institute pilot project of the acceleration of translation research", Clin. Cancer Res., 15(17):5323-5337 (2009).
Morgan et al., "High Efficiency TCR gene transfer into Primary human lymphocytes affords avid recognition of malenoma tumor antigen glycoprotein 100 and does not alter the recognition of autologous melanoma antigens", J. Immunol, 171:3287-3295 (2003).
Chames et al., "Direct selection of a human antibody fragment directed against the tumor T-cell epitope HLA-A1-MAGE-A1 from a nonimmunized phage-Fab library", PNAS, 97(14):7969-7974 (2000).
Andersen et al., "A recombinant antibody with the antigen-specific, major histocompatibility complex-restricted specificity of T cells", PNAS, USA, 93:1820-1824 (1996).
Rosenberg et al., "Cancer Immunotherapy: moving beyond current vaccines", Nature Medicine, 10(9):909-915 (2004).
Zhu et al., "Visualization of $p53_{264-272}$/HLA-A*0201 Complexes naturally presented on tumor cell surface by a multimetric soluble single-chain T cell Receptor", J. Immunol., 176:3223-3232 (2006).

* cited by examiner

*Primary Examiner* — Zachary Skelding
(74) *Attorney, Agent, or Firm* — Sughrue Mion, PLLC

(57) ABSTRACT

A method has been developed to efficiently proliferate and culture a CTL specific to WT1 peptides under limiting dilution conditions. Utilizing this method, CTLs capable of recognizing both a state where a wildtype WT1 specific peptide is presented by HLA-A*24:02 and a state where a mutant WT1 specific peptide is presented by HLA-A*24:02 have been successfully obtained.

18 Claims, 19 Drawing Sheets

TCR α-CHAIN (A12-3)

TCR β-CHAIN (B5-1)

FIG. 15

37-F8 TCR β-CHAIN

LEADER SEQUENCE    TRBV5-1*01

MGSRLLCWVLLCLLGAGPVKAGVTQTPRYLIKTRGQQVTLSCSPISGHRSVSWYQQTPGQGLQF
                                          CDR1

TRBD2*02  TRBJ2-5*01
LFEYFSETQRNKGNFPGRFSGRQFSNSRSEMNVSTLELGDSALYLCASSYGERERKGETQYFGPG
     CDR2    TRBC2                                CDR3

TRLLVLEDLKNVFPPEVAVFEPSEAEISHTQKATLVCLATGFYPDHVELSWWVNGKEVHSGVST

DPQPLKEQPALNDSRYCLSSRLRVSATFWQNPRNHFRCQVQFYGLSENDEWTQDRAKPVTQIV

SAEAWGRADCGFTSESYQQGVLSATILYEILLGKATLYAVLVSALVLMAMVKRKDSRG*
                                          TM

SEQUENCE LISTING

<160> NUMBER OF SEQ ID NOS: 18

<210> SEQ ID NO 1
<211> LENGTH: 6
<212> TYPE: PRT
<213> ORGANISM: Homo sapiens
<220> FEATURE:
<221> NAME/KEY: SITE
<222> LOCATION: (1)..(6)
<223> OTHER INFORMATION: CDR1 of Alpha Chain

<400> SEQUENCE: 1

Asn Ser Ala Phe Gln Tyr
1               5

<210> SEQ ID NO 2
<211> LENGTH: 6
<212> TYPE: PRT
<213> ORGANISM: Homo sapiens
<220> FEATURE:
<221> NAME/KEY: SITE
<222> LOCATION: (1)..(6)
<223> OTHER INFORMATION: CDR2 of Alpha Chain

<400> SEQUENCE: 2

Thr Tyr Ser Ser Gly Asn
1               5

<210> SEQ ID NO 3
<211> LENGTH: 16
<212> TYPE: PRT
<213> ORGANISM: Homo sapiens
<220> FEATURE:
<221> NAME/KEY: SITE
<222> LOCATION: (1)..(16)
<223> OTHER INFORMATION: CDR3 of Alpha Chain

<400> SEQUENCE: 3

Cys Ala Thr Ser Asn Ala Gly Gly Thr Ser Tyr Gly Lys Leu Thr Phe
1               5                   10                  15

<210> SEQ ID NO 4
<211> LENGTH: 120
<212> TYPE: PRT
<213> ORGANISM: Homo sapiens
<220> FEATURE:
<221> NAME/KEY: SITE
<222> LOCATION: (1)..(120)
<223> OTHER INFORMATION: Variable Region of Alpha Chain

<400> SEQUENCE: 4

Trp Val Trp Ser Gln Gln Lys Glu Val Glu Gln Asp Pro Gly Pro Leu
1               5                   10                  15

Ser Val Pro Glu Gly Ala Ile Val Ser Leu Asn Cys Thr Tyr Ser Asn
            20                  25                  30

Ser Ala Phe Gln Tyr Phe Met Trp Tyr Arg Gln Tyr Ser Arg Lys Gly
        35                  40                  45

Pro Glu Leu Leu Met Tyr Thr Tyr Ser Ser Gly Asn Lys Glu Asp Gly
    50                  55                  60

Arg Phe Thr Ala Gln Val Asp Lys Ser Ser Lys Tyr Ile Ser Leu Phe
65                  70                  75                  80

Ile Arg Asp Ser Gln Pro Ser Asp Ser Ala Thr Tyr Leu Cys Ala Thr
                85                  90                  95

Ser Asn Ala Gly Gly Thr Ser Tyr Gly Lys Leu Thr Phe Gly Gln Gly
            100                 105                 110

Thr Ile Leu Thr Val His Pro Asn
                115                 120

<210> SEQ ID NO 5
<211> LENGTH: 5
<212> TYPE: PRT
<213> ORGANISM: Homo sapiens
<220> FEATURE:
<221> NAME/KEY: SITE
<222> LOCATION: (1)..(5)
<223> OTHER INFORMATION: CDR1 of Beta Chain

<400> SEQUENCE: 5

Ser Gly His Arg Ser
1               5

<210> SEQ ID NO 6
<211> LENGTH: 6
<212> TYPE: PRT
<213> ORGANISM: Homo sapiens
<220> FEATURE:
<221> NAME/KEY: SITE
<222> LOCATION: (1)..(6)
<223> OTHER INFORMATION: CDR2 of Beta Chain

<400> SEQUENCE: 6

Tyr Phe Ser Glu Thr Gln
1               5

<210> SEQ ID NO 7
<211> LENGTH: 17
<212> TYPE: PRT
<213> ORGANISM: Homo sapiens
<220> FEATURE:
<221> NAME/KEY: SITE
<222> LOCATION: (1)..(17)
<223> OTHER INFORMATION: CDR3 of Beta Chain

<400> SEQUENCE: 7

Cys Ala Ser Ser Tyr Gly Glu Arg Glu Arg Lys Gly Glu Thr Gln Tyr
1               5                   10                  15
Phe

<210> SEQ ID NO 8
<211> LENGTH: 120
<212> TYPE: PRT
<213> ORGANISM: Homo sapiens
<220> FEATURE:
<221> NAME/KEY: SITE
<222> LOCATION: (1)..(120)
<223> OTHER INFORMATION: Variable Region of Beta Chain

<400> SEQUENCE: 8

Gly Pro Val Lys Ala Gly Val Thr Gln Thr Pro Arg Tyr Leu Ile Lys
1               5                   10                  15

Thr Arg Gly Gln Gln Val Thr Leu Ser Cys Ser Pro Ile Ser Gly His
            20                  25                  30

Arg Ser Val Ser Trp Tyr Gln Gln Thr Pro Gly Gln Gly Leu Gln Phe
        35                  40                  45

Leu Phe Glu Tyr Phe Ser Glu Thr Gln Arg Asn Lys Gly Asn Phe Pro
    50                  55                  60

Gly Arg Phe Ser Gly Arg Gln Phe Ser Asn Ser Arg Ser Glu Met Asn
65                  70                  75                  80

Val Ser Thr Leu Glu Leu Gly Asp Ser Ala Leu Tyr Leu Cys Ala Ser

```
                        85                  90                  95
Ser Tyr Gly Glu Arg Glu Arg Lys Gly Glu Thr Gln Tyr Phe Gly Pro
                100                 105                 110

Gly Thr Arg Leu Leu Val Leu Glu
        115                 120

<210> SEQ ID NO 9
<211> LENGTH: 834
<212> TYPE: DNA
<213> ORGANISM: Homo sapiens
<220> FEATURE:
<221> NAME/KEY: CDS
<222> LOCATION: (1)..(834)
<223> OTHER INFORMATION: Alpha Chain

<400> SEQUENCE: 9 atg atg aaa tcc ttg aga gtt tta ctg gtg atc ctg tgg ctt cag tta    48
Met Met Lys Ser Leu Arg Val Leu Leu Val Ile Leu Trp Leu Gln Leu
1               5                   10                  15 agc tgg gtt tgg agc caa cag aag gag gtg gag cag gat cct gga cca    96
Ser Trp Val Trp Ser Gln Gln Lys Glu Val Glu Gln Asp Pro Gly Pro
            20                  25                  30 ctc agt gtt cca gag gga gcc att gtt tct ctc aac tgc act tac agc   144
Leu Ser Val Pro Glu Gly Ala Ile Val Ser Leu Asn Cys Thr Tyr Ser
        35                  40                  45 aac agt gct ttt caa tac ttc atg tgg tac aga cag tat tcc aga aaa   192
Asn Ser Ala Phe Gln Tyr Phe Met Trp Tyr Arg Gln Tyr Ser Arg Lys
    50                  55                  60 ggc cct gag ttg ctg atg tac aca tac tcc agt ggt aac aaa gaa gat   240
Gly Pro Glu Leu Leu Met Tyr Thr Tyr Ser Ser Gly Asn Lys Glu Asp
65                  70                  75                  80 gga agg ttt aca gca cag gtc gat aaa tcc agc aag tat atc tcc ttg   288
Gly Arg Phe Thr Ala Gln Val Asp Lys Ser Ser Lys Tyr Ile Ser Leu
                85                  90                  95 ttc atc aga gac tca cag ccc agt gat tca gcc acc tac ctc tgt gca   336
Phe Ile Arg Asp Ser Gln Pro Ser Asp Ser Ala Thr Tyr Leu Cys Ala
            100                 105                 110 act tct aat gct ggt ggt act agc tat gga aag ctg aca ttt gga caa   384
Thr Ser Asn Ala Gly Gly Thr Ser Tyr Gly Lys Leu Thr Phe Gly Gln
        115                 120                 125 ggg acc atc ttg act gtc cat cca aat atc cag aac cct gac cct gcc   432
Gly Thr Ile Leu Thr Val His Pro Asn Ile Gln Asn Pro Asp Pro Ala
    130                 135                 140 gtg tac cag ctg aga gac tct aaa tcc agt gac aag tct gtc tgc cta   480
Val Tyr Gln Leu Arg Asp Ser Lys Ser Ser Asp Lys Ser Val Cys Leu
145                 150                 155                 160 ttc acc gat ttt gat tct caa aca aat gtg tca caa agt aag gat tct   528
Phe Thr Asp Phe Asp Ser Gln Thr Asn Val Ser Gln Ser Lys Asp Ser
                165                 170                 175 gat gtg tat atc aca gac aaa act gtg cta gac atg agg tct atg gac   576
Asp Val Tyr Ile Thr Asp Lys Thr Val Leu Asp Met Arg Ser Met Asp
            180                 185                 190 ttc aag agc aac agt gct gtg gcc tgg agc aac aaa tct gac ttt gca   624
Phe Lys Ser Asn Ser Ala Val Ala Trp Ser Asn Lys Ser Asp Phe Ala
        195                 200                 205 tgt gca aac gcc ttc aac aac agc att att cca gaa gac acc ttc ttc   672
Cys Ala Asn Ala Phe Asn Asn Ser Ile Ile Pro Glu Asp Thr Phe Phe
    210                 215                 220 ccc agc cca gaa agt tcc tgt gat gtc aag ctg gtc gag aaa agc ttt   720
Pro Ser Pro Glu Ser Ser Cys Asp Val Lys Leu Val Glu Lys Ser Phe
225                 230                 235                 240
```

```
gaa aca gat acg aac cta aac ttt caa aac ctg tca gtg att ggg ttc    768
Glu Thr Asp Thr Asn Leu Asn Phe Gln Asn Leu Ser Val Ile Gly Phe
                245                 250                 255 cga atc ctc ctc ctg aaa gtg gcc ggg ttt aat ctg ctc atg acg ctg    816
Arg Ile Leu Leu Leu Lys Val Ala Gly Phe Asn Leu Leu Met Thr Leu
            260                 265                 270 cgg ctg tgg tcc agc tga                                             834
Arg Leu Trp Ser Ser
        275
```

<210> SEQ ID NO 10
<211> LENGTH: 277
<212> TYPE: PRT
<213> ORGANISM: Homo sapiens

<400> SEQUENCE: 10

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Thr Ser Asn Ala Gly Gly Thr Ser Tyr Gly Lys Leu Thr Phe Gly Gln
        115                 120                 125

Gly Thr Ile Leu Thr Val His Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 11
<211> LENGTH: 945
<212> TYPE: DNA

<213> ORGANISM: Homo sapiens
<220> FEATURE:
<221> NAME/KEY: CDS
<222> LOCATION: (1)..(945)
<223> OTHER INFORMATION: Beta Chain

<400> SEQUENCE: 11

```
atg ggc tcc agg ctg ctc tgt tgg gtg ctg ctt tgt ctc ctg gga gca      48
Met Gly Ser Arg Leu Leu Cys Trp Val Leu Leu Cys Leu Leu Gly Ala
 1               5                  10                  15 ggc cca gta aag gct gga gtc act caa act cca aga tat ctg atc aaa      96
Gly Pro Val Lys Ala Gly Val Thr Gln Thr Pro Arg Tyr Leu Ile Lys
             20                  25                  30 acg aga gga cag caa gtg aca ctg agc tgc tcc cct atc tct ggg cat     144
Thr Arg Gly Gln Gln Val Thr Leu Ser Cys Ser Pro Ile Ser Gly His
         35                  40                  45 agg agt gta tcc tgg tac caa cag acc cca gga cag ggc ctt cag ttc     192
Arg Ser Val Ser Trp Tyr Gln Gln Thr Pro Gly Gln Gly Leu Gln Phe
     50                  55                  60 ctc ttt gaa tac ttc agt gag aca cag aga aac aaa gga aac ttc cct     240
Leu Phe Glu Tyr Phe Ser Glu Thr Gln Arg Asn Lys Gly Asn Phe Pro
 65                 70                  75                  80 ggt cga ttc tca ggg cgc cag ttc tct aac tct cgc tct gag atg aat     288
Gly Arg Phe Ser Gly Arg Gln Phe Ser Asn Ser Arg Ser Glu Met Asn
                 85                  90                  95 gtg agc acc ttg gag ctg ggg gac tcg gcc ctt tat ctt tgc gcc agc     336
Val Ser Thr Leu Glu Leu Gly Asp Ser Ala Leu Tyr Leu Cys Ala Ser
            100                 105                 110 agc tat ggg gag cgg gag agg aag gga gag acc cag tac ttc ggg cca     384
Ser Tyr Gly Glu Arg Glu Arg Lys Gly Glu Thr Gln Tyr Phe Gly Pro
        115                 120                 125 ggc acg cgg ctc ctg gtg ctc gag gac ctg aaa aac gtg ttc cca ccc     432
Gly Thr Arg Leu Leu Val Leu Glu Asp Leu Lys Asn Val Phe Pro Pro
    130                 135                 140 gag gtc gct gtg ttt gag cca tca gaa gca gag atc tcc cac acc caa     480
Glu Val Ala Val Phe Glu Pro Ser Glu Ala Glu Ile Ser His Thr Gln
145                 150                 155                 160 aag gcc aca ctg gtg tgc ctg gcc aca ggc ttc tac ccc gac cac gtg     528
Lys Ala Thr Leu Val Cys Leu Ala Thr Gly Phe Tyr Pro Asp His Val
                165                 170                 175 gag ctg agc tgg tgg gtg aat ggg aag gag gtg cac agt ggg gtc agc     576
Glu Leu Ser Trp Trp Val Asn Gly Lys Glu Val His Ser Gly Val Ser
            180                 185                 190 aca gac ccg cag ccc ctc aag gag cag ccc gcc ctc aat gac tcc aga     624
Thr Asp Pro Gln Pro Leu Lys Glu Gln Pro Ala Leu Asn Asp Ser Arg
        195                 200                 205 tac tgc ctg agc agc cgc ctg agg gtc tcg gcc acc ttc tgg cag aac     672
Tyr Cys Leu Ser Ser Arg Leu Arg Val Ser Ala Thr Phe Trp Gln Asn
    210                 215                 220 ccc cgc aac cac ttc cgc tgt caa gtc cag ttc tac ggg ctc tcg gag     720
Pro Arg Asn His Phe Arg Cys Gln Val Gln Phe Tyr Gly Leu Ser Glu
225                 230                 235                 240 aat gac gag tgg acc cag gat agg gcc aaa cct gtc acc cag atc gtc     768
Asn Asp Glu Trp Thr Gln Asp Arg Ala Lys Pro Val Thr Gln Ile Val
                245                 250                 255 agc gcc gag gcc tgg ggt aga gca gac tgt ggc ttc acc tcc gag tct     816
Ser Ala Glu Ala Trp Gly Arg Ala Asp Cys Gly Phe Thr Ser Glu Ser
            260                 265                 270 tac cag caa ggg gtc ctg tct gcc acc atc ctc tat gag atc ttg cta     864
Tyr Gln Gln Gly Val Leu Ser Ala Thr Ile Leu Tyr Glu Ile Leu Leu
        275                 280                 285
```

```
ggg aag gcc acc ttg tat gcc gtg ctg gtc agt gcc ctc gtg ctg atg    912
Gly Lys Ala Thr Leu Tyr Ala Val Leu Val Ser Ala Leu Val Leu Met
    290                 295                 300 gcc atg gtc aag aga aag gat tcc aga ggc tag                        945
Ala Met Val Lys Arg Lys Asp Ser Arg Gly
305                 310

<210> SEQ ID NO 12
<211> LENGTH: 314
<212> TYPE: PRT
<213> ORGANISM: Homo sapiens

<400> SEQUENCE: 12

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Tyr Gly Glu Arg Glu Arg Lys Gly Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 13
```

<211> LENGTH: 365
<212> TYPE: PRT
<213> ORGANISM: Homo sapiens

<400> SEQUENCE: 13

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Ser Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Val Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Asn Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 14
<211> LENGTH: 240
<212> TYPE: PRT

<213> ORGANISM: Homo sapiens

<400> SEQUENCE: 14

```
Trp Val Trp Ser Gln Gln Lys Glu Val Gln Asp Pro Gly Pro Leu
1               5                  10                  15

Ser Val Pro Glu Gly Ala Ile Val Ser Leu Asn Cys Thr Tyr Ser Asn
            20                  25                  30

Ser Ala Phe Gln Tyr Phe Met Trp Tyr Arg Gln Tyr Ser Arg Lys Gly
        35                  40                  45

Pro Glu Leu Leu Met Tyr Thr Tyr Ser Ser Gly Asn Lys Glu Asp Gly
    50                  55                  60

Arg Phe Thr Ala Gln Val Asp Lys Ser Ser Lys Tyr Ile Ser Leu Phe
65                  70                  75                  80

Ile Arg Asp Ser Gln Pro Ser Asp Ser Ala Thr Tyr Leu Cys Ala Thr
                85                  90                  95

Ser Asn Ala Gly Gly Thr Ser Tyr Gly Lys Leu Thr Phe Gly Gln Gly
            100                 105                 110

Thr Ile Leu Thr Val His Pro Asn Ile Gln Asn Pro Asp Pro Ala Val
        115                 120                 125

Tyr Gln Leu Arg Asp Ser Lys Ser Ser Asp Lys Ser Val Cys Leu Phe
    130                 135                 140

Thr Asp Phe Asp Ser Gln Thr Asn Val Ser Gln Ser Lys Asp Ser Asp
145                 150                 155                 160

Val Tyr Ile Thr Asp Lys Thr Val Leu Asp Met Arg Ser Met Asp Phe
                165                 170                 175

Lys Ser Asn Ser Ala Val Ala Trp Ser Asn Lys Ser Asp Phe Ala Cys
            180                 185                 190

Ala Asn Ala Phe Asn Asn Ser Ile Ile Pro Glu Asp Thr Phe Phe Pro
        195                 200                 205

Ser Pro Glu Ser Ser Cys Asp Val Lys Leu Val Glu Lys Ser Phe Glu
    210                 215                 220

Thr Asp Thr Asn Leu Asn Phe Gln Asn Leu Ser Val Ile Gly Phe Arg
225                 230                 235                 240
```

<210> SEQ ID NO 15
<211> LENGTH: 269
<212> TYPE: PRT
<213> ORGANISM: Homo sapiens

<400> SEQUENCE: 15

```
Gly Pro Val Lys Ala Gly Val Thr Gln Thr Pro Arg Tyr Leu Ile Lys
1               5                  10                  15

Thr Arg Gly Gln Gln Val Thr Leu Ser Cys Ser Pro Ile Ser Gly His
            20                  25                  30

Arg Ser Val Ser Trp Tyr Gln Gln Thr Pro Gly Gln Gly Leu Gln Phe
        35                  40                  45

Leu Phe Glu Tyr Phe Ser Glu Thr Gln Arg Asn Lys Gly Asn Phe Pro
    50                  55                  60

Gly Arg Phe Ser Gly Arg Gln Phe Ser Asn Ser Arg Ser Glu Met Asn
65                  70                  75                  80

Val Ser Thr Leu Glu Leu Gly Asp Ser Ala Leu Tyr Leu Cys Ala Ser
                85                  90                  95

Ser Tyr Gly Glu Arg Glu Arg Lys Gly Glu Thr Gln Tyr Phe Gly Pro
            100                 105                 110

Gly Thr Arg Leu Leu Val Leu Glu Asp Leu Lys Asn Val Phe Pro Pro
```

```
              115                 120                 125
Glu Val Ala Val Phe Glu Pro Ser Glu Ala Glu Ile Ser His Thr Gln
            130                 135                 140

Lys Ala Thr Leu Val Cys Leu Ala Thr Gly Phe Tyr Pro Asp His Val
145                 150                 155                 160

Glu Leu Ser Trp Trp Val Asn Gly Lys Glu Val His Ser Gly Val Ser
                165                 170                 175

Thr Asp Pro Gln Pro Leu Lys Glu Gln Pro Ala Leu Asn Asp Ser Arg
            180                 185                 190

Tyr Cys Leu Ser Ser Arg Leu Arg Val Ser Ala Thr Phe Trp Gln Asn
            195                 200                 205

Pro Arg Asn His Phe Arg Cys Gln Val Gln Phe Tyr Gly Leu Ser Glu
            210                 215                 220

Asn Asp Glu Trp Thr Gln Asp Arg Ala Lys Pro Val Thr Gln Ile Val
225                 230                 235                 240

Ser Ala Glu Ala Trp Gly Arg Ala Asp Cys Gly Phe Thr Ser Glu Ser
                245                 250                 255

Tyr Gln Gln Gly Val Leu Ser Ala Thr Ile Leu Tyr Glu
            260                 265

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Cys Tyr Thr Trp Asn Gln Met Asn Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Cys Met Thr Trp Asn Gln Met Asn Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Arg Tyr Leu Arg Asp Gln Gln Leu Leu
1               5
```

T CELL RECEPTOR AND USES THEREOF

This application claims priority based on Japanese Patent Application No. 2013-015844 filed Jan. 30, 2013, the contents of all of which are incorporated herein by reference in their entirety.

BACKGROUND OF THE INVENTION

Field of the Invention

The present invention relates to: an isolated T cell receptor (hereinafter referred to as "TCR") capable of recognizing a cancer antigen restricted to HLA-A*24:02; and the uses of the TCR for detection of a cancer antigen restricted to HLA-A*24:02, for cancer treatment, and for other purposes.

Related Background Art

In Japan, approximately 350,000 people die of cancers every year, and approximately 700,000 are newly diagnosed as cancers. In the cancer treatment, mainly three standard treatments are given: surgery, anticancer drug, and radiation therapy. When no improvement is observed after such treatments, there is no choice but palliative care for relieving various cancer-caused pains. In such cancer treatment situations in Japan, patients themselves or families of the patients are called "cancer refugees" from their endeavor searching for further treatments, bringing about a social problem.

Currently, cancer vaccination is actively studied as an intermediate treatment between the standard treatment and the palliative care. The cancer vaccination is a treatment given in order to eliminate or regress cancer by activating the immunity of the patients themselves. Provenge (Sipuleucel-T) approved by the United State Food and Drug Administration (FDA) in April, 2010, is one used in the cancer vaccination. Provenge is approved for patients with prostate cancer that is metastatic and hormonal therapy resistant. In the treatment method with Provenge, peripheral blood of the patient is stimulated using a PAP (prostatic-acid phosphatase) protein over-expressed in most cases of prostate cancer, and then Provenge is transferred into the body of the patient. Whether the cancer vaccination succeeds or not depends on the immunity of the patients themselves. For this reason, it is believed that the cancer vaccination is more effective if performed before the symptom of the patient is worsened by various standard treatments. In the future, such a cancer vaccination is desirably approved as a treatment choice in place of the anticancer drug treatment or as a treatment method applicable in combination with an anticancer drug.

The cancer vaccination is roughly classified into two: an antigen non-specific treatment method and an antigen specific treatment method. An antigen non-specific immunotherapy has started since 1970s using picibanil, Krestin, killed *Mycobacterium tuberculosis* (BCG-CWS), or the like having an immunostimulating action. In 1980s, immunotherapies were performed using cytokines such as IL-2, and LAK (lymphokine activated killer cell) therapies were performed in which T cells non-specifically proliferated were returned into the body of the patient. However, any of these failed to clearly produce clinical effects, and are not covered by health insurance.

It was reported in 1991 that cytotoxic T lymphocytes (hereinafter referred to as "CTLs"), which were separated from a patient and proliferated, specifically recognized cancer antigens called MAGE (melanoma antigen) expressed at high level on cancer cells, and killed the cancer cells (Science 1991. 254: 1643-1647). Moreover, in 1994, there was a report on a mechanism of CTLs to recognize and kill peptide fragments presented by MHC (Major Histocompatibility Complex, called HLA in human) on cancer cell surfaces (Science 1994; 264: 716-719). After that, researchers all over the world identified various peptide fragments presented by HLA. In 1996, Altman et al. developed MHC tetramer reagents capable of detecting specific CTLs (Science, 1996; 274: 94-96). This made it possible to directly demonstrate CTL detection which has been so far verified only indirectly by $^{51}$Cr release assay. The melanoma-targeting cancer peptide vaccination reported in 1998 produced surprising clinical outcome, and thus cancer immunotherapy has flourished at once (Nat Med, 1998; 4: 321-327). Since then, cancer peptide vaccinations through subcutaneous or intradermal inoculation with peptides have been in progress on a worldwide scale.

In 2004, Rosenberg et al. reported that the response rate by cancer vaccination was lower than expected, and cautioned that the subjects of the clinical trials were terminal cancer patients (Nat Med, 2004; 10: 909-915). This is because whether or not CTLs that attack cancer cells in the body of the patients after inoculation with a peptide vaccine are proliferated as hoped depends on the immunity of the patients themselves. Hence, it seems natural that if the immunity is greatly lowered due to chemotherapy or radiation therapy, the response rate is also lowered. Patients inoculated with a peptide vaccine require steps of: activating T cells by causing dendritic cells or macrophages, which are called antigen-presenting cells, residing in the vicinity of the inoculation site to incorporate the peptide and present it to MHC on the cell surface; and further activating T cells by recruiting antigen-presenting cells from regional lymph nodes also. In patients with the immunity greatly lowered due to an anticancer drug or radiation therapy, presumably the number of antigen-presenting cells is reduced, and that the antigen-presenting cells do not function properly. This may limit the anticancer effect. For this reason, a dendritic cell treatment is performed: such antigen-presenting cells as dendritic cells or macrophages are separated and cultured to proliferate in vitro, and patients are inoculated with the antigen-presenting cells ready to present the antigen. However, even if such a treatment is performed, the effect is thought to be limited in some cases as in peptide vaccination because patients having the immunity lowered do not have a sufficient amount of T cells in the first place, or because the T cells are not activated sufficiently.

Then, in order to compensate for the shortcomings of the peptide vaccine and the dendritic cell treatment, a CTL treatment is performed in which T cells activated in vitro are returned into the body of the patient. For this method, a dedicated cell processing center (CPC) is required to transfer the cells into the blood. Since complicated cell-culturing operations are repeated, developments of, for example, automated culture system and the like are accordingly in progress. However, quite difficult culture techniques are required regarding how specific CTLs are proliferated in vitro efficiently within a short period of time.

T cells act by recognizing and binding to a complex of a MHC molecule and an antigenic peptide (hereinafter referred to as "MHC/peptide complex") presented on the cell surface of targets such as antigen-presenting cells, cancer cells, and infected cells, via a TCR expressed on the surface of the T cells. It is believed that CD8 positive T cells bind only to a MHC class I molecule/antigenic peptide complex (MHC class I restriction), and that CD4 positive T cells bind only to a MHC class II molecule/antigenic peptide complex (MHC class II restriction). While MHC class I molecules are expressed on most of nucleated cells and platelets, MHC class II molecules are expressed only on limited types of cells. For this reason, CD4 positive T cells can bind to dendritic cells, B cells, activating T cells, and the like expressing MHC class II molecules, but cannot directly binds to others such as tumor cells and infected cells. Nevertheless, it has been demonstrated that when a TCR gene derived from CD8 positive T cells (CTLs) believed to be restricted to MHC class I is introduced by genetic manipulation into CD4 positive CD8 negative T cells believed to be restricted to MHC class II, the T cells are activated by reacting in a CD8-molecule independent manner with antigen-presenting cells pulsed with a corresponding antigen, demonstrating a cytotoxic activity. Moreover, it has been reported that cancer can be specifically regressed by introducing a TCR gene derived from cancer antigen specific CTL into peripheral blood lymphocytes having a non-specific anti-tumor activity (J. Immunol., 2003; 171: 3287-3295). Accordingly, there have been active attempts to conduct TCR gene therapy in which TCR genes isolated from specific CTLs are artificially expressed in peripheral lymphocytes, and artificial CTLs are prepared to be returned into the body of the patient (Science 2006; 314: 126-129).

For approximately 20 years, quite a large number of peptide fragments (CTL epitopes) were identified from proteins associated with cancers, infectious diseases, autoimmune diseases, and engraftment. Even if CTL epitopes are derived from the same protein, the type of presented peptide fragments varies, depending on the HLA type. This is generally called HLA restriction of CTL epitope.

In a cancer vaccination, selection of a cancer antigen from which a CTL epitope is derived is a very important point for the target patient. A CTL epitope is desirably restricted to an HLA type widely possessed within human races, among extremely diverse HLA types. For example, while 1527 proteins are registered for HLA-A, there are 21 genotypes for the HLA-A type with a frequency of 0.1% or higher according to the paper which analyzed the HLA type of 1018 Japanese (Immunogenetics, 2005; 57: 717-729). Among these, HLA-A*24:02 was detected at a frequency of 36.2%, which suggests that 60 to 70% of Japanese have the HLA type. Accordingly, it is very meaningful to identify a CTL epitope restricted to an HLA type with such a high frequency.

While a great number of CTL epitopes have been reported, the result of evaluating 75 CTL epitopes specific to cancer antigen on the basis of nine criteria was reported in 2009 (Clin. Cancer Res., 2009; 15: 5323-5337). The nine criteria include (a) therapeutic function, (b) immunogenicity, (c) role of the antigen in oncogenicity, (d) specificity, (e) expression level and percent of antigen-positive cells, (f) stem cell expression, (g) number of patients with antigen-positive cancers, (h) number of antigenic epitopes, and (i) cellular location of antigen expression. According to this report, WT1 is the most promising CTL epitope in the cancer vaccination among the 75 cancer antigens.

Regarding what cancer antigen a vaccination to a target patient should target, it is desirable to carry out a diagnosis before the vaccination is started. For example, in performing HLA-A*24:02-restricted WT1 peptide vaccination, it is a prerequisite that the HLA type of the target patient should be HLA-A*24:02. The HLA type examination is an essential examination for organ transplantation or bone marrow transplantation, and is conducted in various facilities. In addition, since it is essential that the WT1 peptide restricted to HLA-A*24:02 should be presented on the target cancer cell surface to be recognized by CTLs, this condition is most desirably proved in order to perform the HLA-A*24:02-restricted WT1 peptide vaccination. Nevertheless, currently, no examination method is available for directly proving the condition; instead, an indirect examination is conducted. For example, utilized for WT1 are: a method in which the level of WT1 mRNA expressed is checked by quantitative PCR using a biopsy sample, a method in which an expression of a WT1 protein in cells is checked using an anti-WT1 antibody, and a method in which an HLA expression is checked using an anti-HLA antibody. Tools which have been studied for the direct proving include antibodies for specifically recognizing a state where a peptide binds to MHC (hereinafter referred to as "anti-pMHC antibody"), TCR tetramers utilizing TCR, scTCR (single chain TCR) multimers utilizing single chain TCR, and the like.

Regarding the anti-pMHC antibody, there were a report in 1989 on an antibody specifically recognizing MHC class II presenting a peptide (Nature, 1989; 338: 765-768), and a report in 1997 on an antibody recognizing a state where an OVA (ovalbumin)-derived peptide is presented by a mouse MHC class I molecule H-2K$^b$ (Immunity, 1997; 6: 715-726). Many researchers have started attempting to obtain similar antibodies.

Molecules constituting a MHC/peptide complex are in such a state that a MHC having a molecular weight of approximately 45 kDa is non-covalently bonded to β2m (β2-microglobulin) of approximately 12 kDa. For example, in a case of a peptide presented by MHC class I, approximately 8 to 11 amino acids are bonded. It is very difficult to obtain, by hybridoma technology, antibodies specifically recognizing only the difference in presented peptides. In fact, only several antibodies were reported in the past 20 years.

For example, there was a report in 1996 that an antibody against a MHC/peptide complex was obtained by the phage display technology using a library derived from an immunized mouse (PNAS, 1996; 93: 1820-1824). Then, there was a report in 2000 that an antibody specific to an HLA-A1/MAGE-A1 complex was obtained from a library derived from non-immunized human (PNAS, 2000; 97: 7969-7974). Antibodies obtained in this manner can exhibit a reactivity when artificially bound to a peptide on the cell surface. However, it is known to be very difficult to develop an antibody capable of exhibiting a reactivity when an endogenous peptide is presented in a natural state on the cell surface. CTLs are believed to demonstrate a cytotoxic activity when activated by specifically binding to approximately several to 10 MHC/peptide complexes that the CTLs can specifically recognize among several tens of thousands of MHC/peptide complexes expressed on the surface of one target cell. In order to detect this phenomenon without using specific CTLs, a reagent similarly capable of binding to approximately several to 10 MHC/peptide complexes per cell has to be developed and detected with an analyzer. Even in a case for example where proteins expressed on the cell surface are analyzed by flow cytometry using a specific antibody, if less than 100 target proteins are expressed per cell, it is difficult to determine from the analysis result that the molecules of interest are expressed in many cases. It is pointed out that the currently-available analyzers may not have an enough detection sensitivity.

Heretofore, a MHC/peptide complex detection system utilizing soluble TCR has been conceived (J Mol Biol, 1994; 242: 655-669). However, its applicability has been considered to be low because it is difficult to obtain α-chain and β-chain proteins constituting the TCR while their conformations as a functional recombinant protein complex are being kept, and because the binding strength is weak between the TCR and the MHC/peptide complex. Nevertheless, as in the case of MHC tetramer reagent synthesis technique, it was reported in 2004 that such a TCR was practically usable in the form of tetramer (Nat Biotechnol, 2004; 22: 1429-1434). In 2006, a reagent capable of specifically detecting a MHC/peptide complex was successfully produced by modifying TCR proteins forming a heterodimer of α-chain and β-chain into a single chain TCR (scTCR) having Vα, Vβ, and Cβ linked to each other, followed by multimerization (J. Immunol. 2006; 176: 3223-3232).

SUMMARY OF THE INVENTION

An object of the present invention is to provide: a TCR capable of recognizing both a state where a wildtype WT1 specific peptide is presented by HLA-A*24:02 and a state where a mutant WT1 specific peptide is presented by HLA-A*24:02; and DNAs encoding the TCR.

Cancer antigen specific CTLs exist only at a very low frequency. In the examination by the present inventors using peripheral blood of healthy subjects, even the existing frequency of CTLs specific to WT1 restricted to the HLA-A*24:02, which was believed to be at a relatively high frequency, was calculated to be 1 in approximately $1 \times 10^7$ of peripheral blood mononuclear cells (PBMCs), which were separated from the peripheral blood according to the conventional method. The result of this calculation indicates that only one WT1 specific CTL exists in approximately 10 mL of the peripheral blood. Accordingly, in order to obtain a CTL having a target TCR gene, some measure should be taken, such as culturing the CTL to proliferate.

In addition, the gene sequence of TCR is very rich in diversity. TCR is a membrane surface protein located on the surface of a T cell, and two types of heterodimer have been identified: one consisting of α-chain/β-chain, and the other consisting of γ-chain/δ-chain. Like the immunoglobulin gene, the TCR gene includes: a V domain generating the diversity of the molecule, called a signal sequence cleaved at the time of the appearance on the cell membrane surface, a variable segment (V: variable), a diversity segment (D: diversity), and a joining segment (J: joining); and a C domain including a constant segment (C: constant) such as an extracellular constant segment, a transmembrane segment, and an intracellular segment. Since these amino acid sequences of T cell differ from one another, TCR is not only an antigen-recognizing molecule, but also a marker of an individual T cell. The diversity of TCR is generated by adoptive rearrangement of the TCR gene. It is known that TCR β- and δ-chains were formed by rearrangement of V-D-J while TCR α- and γ-chains are formed by rearrangement of V-J. Even if the sequences registered in the IMGT® database are linked simply, there are 6,930 combinations for the α-chain with Vα (105 segments), Jα (66 segments), and Cα (1 segment), and there are 12,384 combinations for the β-chain with Vβ (129 segments), Dβ (3 segments), Jβ (16 segments), and Cβ (2 segments). Additionally, regarding the combination of α-chain and β-chain, there are $8.6 \times 10^7$ combinations (nevertheless, since a large number of bases are inserted and/or deleted at a recombination site in each segment, it is difficult to calculate the diversity of T cells accurately. There is a report that the diversity is created as many as $10^{15}$). Thus, in order to identify a correct combination of α-chain and β-chain of a target TCR gene, some measure should be taken to proliferate CTLs having a single type of TCR.

For this, the present inventors first earnestly studied a method for efficiently proliferating and culturing a CTL specific to WT1 peptides under limiting dilution conditions. In this respect, according to the above-described knowledge of the present inventors regarding the existing frequency of the WT1 specific CTL, when PBMCs are dispensed into 96-well plates in such a manner that $1 \times 10^5$ to $5 \times 10^5$ PBMCs are in one well, the number of wells having the target CTL is 0 to 2 per plate. Hence, it is very likely that the CTLs obtained by this method are originated from one CTL. Actually, the present inventors dispensed the aforementioned number of CTLs into 96-well plates and stimulated the CTLs with the WT1 peptide, followed by 2-week culturing to proliferate the CTLs. Then, an analysis was performed using a MHC tetramer reagent. As a result, the inventors successfully obtained CTLs capable of recognizing both a state where a wildtype WT1 specific peptide was presented by HLA-A*24:02 and a state where a mutant WT1 specific peptide was presented by HLA-A*24:02.

The cytotoxic activity of the CTLs thus obtained was examined. As a result, the cytotoxic activity was demonstrated on both a lymphoblastoid cell line to which the wildtype WT1 specific peptide was presented by HLA-A*24:02 and a lymphoblastoid cell line to which the mutant WT1 specific peptide was presented by HLA-A*24:02. Moreover, a repertoire analysis on TCR of the obtained CTL cell population revealed that the Vβ-chain belonged to subgroup Vβ5.1.

Further, the present inventors synthesized cDNA by a reverse transcriptase reaction from the total RNA extracted from the obtained CTL, and then determined the full-length sequences of TCR α-chain and β-chain by PCR. Furthermore, the TCR α-chain and β-chain were expressed in cultured cell lines and analyzed with an HLA-A*24:02 WT1 tetramer reagent. Thereby, a correct combination of α-chain and β-chain capable of specifically recognizing a WT1 peptide presented by HLA-A*24:02 was identified.

It was possible to efficiently detect a transformed cell line expressing the correct combination of α-chain and β-chain with the HLA-A*24:02 WT1 tetramer reagent, while the use of the transformed cell line also made it possible to efficiently detect HLA-A*24:02 WT1 tetramer reagents and cells having WT1 specific peptide presented by HLA-A*24:02.

Thus, the present invention relates to: a TCR capable of recognizing both a state where a wildtype WT1 specific peptide is presented by HLA-A*24:02 and a state where a mutant WT1 specific peptide is presented by HLA-A*24:02; DNAs encoding the TCR; and the uses thereof. More specifically, the present invention provides the following inventions.

(1) An isolated T cell receptor complex comprising:
a T cell receptor α-chain protein having amino acid sequences of SEQ ID NOs: 1 to 3; and
a T cell receptor β-chain protein having amino acid sequences of SEQ ID NOs: 5 to 7.
(2) The T cell receptor complex according to (1), comprising:
a T cell receptor α-chain protein having an amino acid sequence of SEQ ID NO: 4; and
a T cell receptor β-chain protein having an amino acid sequence of SEQ ID NO: 8.
(3) The T cell receptor complex according to (1), comprising:
a T cell receptor α-chain protein having an amino acid sequence of SEQ ID NO: 14; and a T cell receptor β-chain protein having an amino acid sequence of SEQ ID NO: 15.

(4) The T cell receptor complex according to any one of (1) to (3), which is capable of recognizing a wildtype WT1 peptide restricted to HLA-A*24:02 and a mutant WT1 peptide restricted to HLA-A*24:02.

(5) An isolated T cell receptor α-chain protein having amino acid sequences of SEQ ID NOs: 1 to 3.

(6) The T cell receptor α-chain protein according to (5), which has an amino acid sequence of SEQ ID NO: 4.

(7) The T cell receptor α-chain protein according to (5), which has an amino acid sequence of SEQ ID NO: 14.

(8) An isolated T cell receptor β-chain protein having amino acid sequences of SEQ ID NOs: 5 to 7.

(9) The T cell receptor β-chain protein according to (8), which has an amino acid sequence of SEQ ID NO: 8.

(10) The T cell receptor β-chain protein according to (8), which has an amino acid sequence of SEQ ID NO: 15.

(11) An isolated DNA encoding the T cell receptor α-chain protein according to any one of (5) to (7).

(12) An isolated DNA encoding the T cell receptor β-chain protein according to any one of (8) to (10).

(13) A vector comprising and being capable of expressing a DNA of any one of (a) to (c) below:
   (a) the DNA according to (11);
   (b) the DNA according to (12); and
   (c) the DNA according to (11) and the DNA according to (12).

(14) A transformed cell comprising a DNA of any one of (a) to (c) below:
   (a) the DNA according to (11);
   (b) the DNA according to (12); and
   (c) the DNA according to (11) and the DNA according to (12).

(15) A transformed cell comprising the DNA according to (11) and the DNA according to (12), the transformed cell being detectable by a molecule multimerized by binding a wildtype WT1 peptide restricted to HLA-A*24:02 and a molecule multimerized by binding a mutant WT1 peptide restricted to HLA-A*24:02.

(16) The transformed cell according to any one of (14) and (15), which is a lymphocyte.

(17) A pharmaceutical composition for treating a WT1 positive cancer, the pharmaceutical composition comprising the transformed cell according to (16) as an active ingredient.

(18) An isolated antibody capable of specifically binding to a molecule of any one of (a) to (c) below:
   (a) the T cell receptor α-chain protein according to any one of (5) to (7);
   (b) the T cell receptor β-chain protein according to any one of (8) to (10); and
   (c) the T cell receptor complex according to any one of (1) to (4).

(19) A molecule multimerized by binding the T cell receptor complex according to any one of (1) to (4).

(20) A drug for detecting or capturing any one of a wildtype WT1 peptide restricted to HLA-A*24:02 and a mutant WT1 peptide restricted to HLA-A*24:02, the drug comprising the molecule according to (19).

(21) A kit for detecting any one of a wildtype WT1 peptide restricted to HLA-A*24:02 and a mutant WT1 peptide restricted to HLA-A*24:02, the kit comprising at least one component of (a) to (h) below:
   (a) the T cell receptor α-chain protein according to any one of (5) to (7);
   (b) the T cell receptor β-chain protein according to any one of (8) to (10);
   (c) the T cell receptor complex according to anyone of (1) to (4);
   (d) the DNA according to any one of (11) and (12);
   (e) the vector according to (13);
   (f) the transformed cell according to any one of (14) to (16);
   (g) the antibody according to (18); and
   (h) the molecule according to (19).

(22) A quality management method for any one of a molecule multimerized by binding a wildtype WT1 peptide restricted to HLA-A*24:02 and a molecule multimerized by binding a mutant WT1 peptide restricted to HLA-A*24:02, the method comprising a step of checking a reactivity between the molecule and the transformed cell according to any one of (14) to (16).

For the analysis of WT1 specific CTLs in peripheral blood of cancer patients, both a MHC tetramer reagent synthesized using a wildtype WT1 peptide and HLA-A*24:02 and a MHC tetramer reagent synthesized using a mutant WT1 peptide and HLA-A*24:02 have been used to analyze WT1 specific CTLs as an active ingredient in WT1 peptide vaccination. Now, the utilization of the TCR of the present invention makes it possible to efficiently detect both a state where a wildtype WT1 specific peptide is presented by HLA-A*24:02 and a state where a mutant WT1 specific peptide is presented by HLA-A*24:02. Since a ratio of the binding strength between the TCR of the present invention and HLA-A*24:02 wildtype WT1 tetramer reagent to that between the TCR of the present invention and HLA-A*24:02 mutant WT1 tetramer reagent is as small as approximately 2, and the binding strength between the TCR of the present invention; in addition, the HLA-A*24:02 WT1 (wildtype) tetramer reagent is high. Accordingly, the TCR of the present invention has such an advantage that positive and negative can be clearly distinguished from each other. Moreover, the TCR molecules of the present invention and transformed cells thereof are useful for quality management and setting of use conditions of HLA-A*24:02 WT1 tetramer reagents, and also useful as a companion diagnostic agent for checking whether or not cells having a WT1 specific peptide presented by HLA-A*24:02 exist in a biological sample. Furthermore, the TCR molecules of the present invention and the transformed cells are useful as a therapeutic drug for cancers associated with WT1.

BRIEF DESCRIPTION OF THE DRAWINGS

In FIG. 3, the X axis represents the fluorescence intensity (log scale) of an FITC-labeled anti-Vβ antibody, and the Y axis represents the fluorescence intensity (log scale) of a PE-labeled anti-Vβ antibody. In each chart, the lower left quadrant region illustrates a cell population not stained with any antibody, the upper left quadrant region illustrates a cell population stained with the PE-labeled anti-Vβ antibody, the upper right quadrant region illustrates a cell population stained with an anti-Vβ antibody labeled with both of PE and FITC, and the lower right quadrant region illustrates a cell population stained with the FITC-labeled anti-Vβ antibody. The subgroup names of the Vβ region specifically stained with the anti-Vβ antibodies are noted in the charts.

FIG. 15 illustrates a structural feature of β-chain of the TCR specific to HLA-A*24:02 WT1 (SEQ ID NO: 12).

DETAILED DESCRIPTION OF THE PREFERRED EMBODIMENTS

<TCR Complex, TCR α-Chain, TCR β-Chain>

Figure 1A:
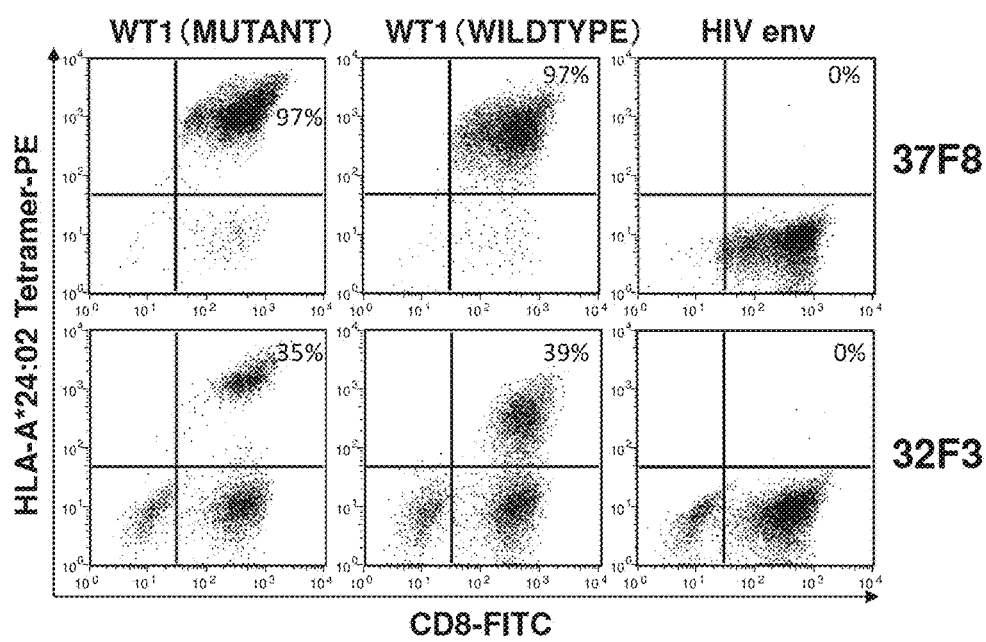
FIG. 1A shows dot plot distribution charts for illustrating a reactivity of two CTL populations (37F8 and 32F3) to MHC tetramer reagents. In the charts, the X axis represents the staining intensity (log scale) of an FITC-labeled anti-CD8 antibody, and the Y axis represents the staining intensity (log scale) of the PE-labeled MHC tetramer reagents. The upper portions of the dot plots indicate the type of MHC tetramer reagent used. The upper right quadrant of each dot plot shows an existing ratio (%) of CTLs positive for the anti-CD8 antibody and positive for the corresponding MHC tetramer reagent inviable cells. The upper charts show the result of 37F8, and the lower charts show the result of 32F3.

The present invention provides a TCR complex comprising a TCR α-chain protein and a TCR β-chain protein. A typical characteristic of the TCR complex of the present invention is to recognize a wildtype WT1 peptide restricted to HLA-A*24:02 and a mutant WT1 peptide restricted to HLA-A*24:02.

In the present invention, "HLA-A*24:02" is a type that Japanese have most frequently, encoded at the A locus of human leukocyte antigen (HLA) class I molecules, classified in A*24 according to the serological HLA typing, and classified as a subtype having amino acid mutation (the amino acid sequence of HLA-A*24:02 is shown in SEQ ID NO: 13). Moreover, the "wildtype WT1 peptide restricted to HLA-A*24:02" and the "mutant WT1 peptide restricted to HLA-A*24:02" mean to include both a case where these peptides exist on the cell surface, and a case where the peptides exist as isolated or purified molecules (for example, molecules having these peptides restricted to a multimerized TCR complex).

In the present invention, a "wildtype WT1 peptide" means "CMTWNQMNL" (SEQ ID NO: 9), and a "mutant WT1 peptide" means "CYTWNQMNL" (SEQ ID NO: 10). The mutant WT1 peptide is obtained by substituting the second methionine (M) of the wildtype WT1 peptide with tyrosine (Y), so that the binding to HLA and the stability are increased, and a WT1 specific anti-tumor immune response can be more strongly induced. In addition, it has been reported that CTLs induced by a mutant WT1 peptide recognize HLA-A*24:02 presenting a wildtype WT1 peptide and have a cytotoxic activity (Cancer Immunol Immunother, 2002; 51: 614-620). It has been proved that when liver cancer patients are inoculated with such peptide fragments as a vaccine, CTLs thus induced specifically kill the cancer, and several clinical trials have been conducted (PNAS, 2004; 101: 13885-13890). Nevertheless, in clinical trials using the mutant WT1 peptide restricted to HLA-A*24:02, for the analysis of WT1 specific CTLs in peripheral blood of patients, both a MHC tetramer reagent synthesized using a wildtype WT1 peptide and HLA-A*24:02 and a MHC tetramer reagent synthesized using a mutant WT1 peptide and HLA-A*24:02 are used to analyze WT1 specific CTLs as an active ingredient of a WT1 peptide vaccination. The TCR provided by the present invention is characterized by being capable of specifically reacting with both of the HLA-A*24:02 WT1 tetramer reagents.

The present invention also provides a TCR α-chain protein and a TCR β-chain protein constituting the TCR complex. The TCR α-chain protein constituting the TCR complex identified by the present inventors comprises, as complementarity determining regions on a variable region, CDR1 having an amino acid sequence of SEQ ID NO: 1, CDR2 having an amino acid sequence of SEQ ID NO: 2, and CDR3 having an amino acid sequence of SEQ ID NO: 3. Thus, the present invention provides a TCR α-chain protein having amino acid sequences of SEQ ID NOs: 1 to 3. Note that the CDRs in the present invention can be specified by an analysis according to the method described in the literature (Nucleic Acids Res. 2008 Jul. 1; 36 (Web Server issue): W503-W508) with software provided by IMGT®.

Figure 14:
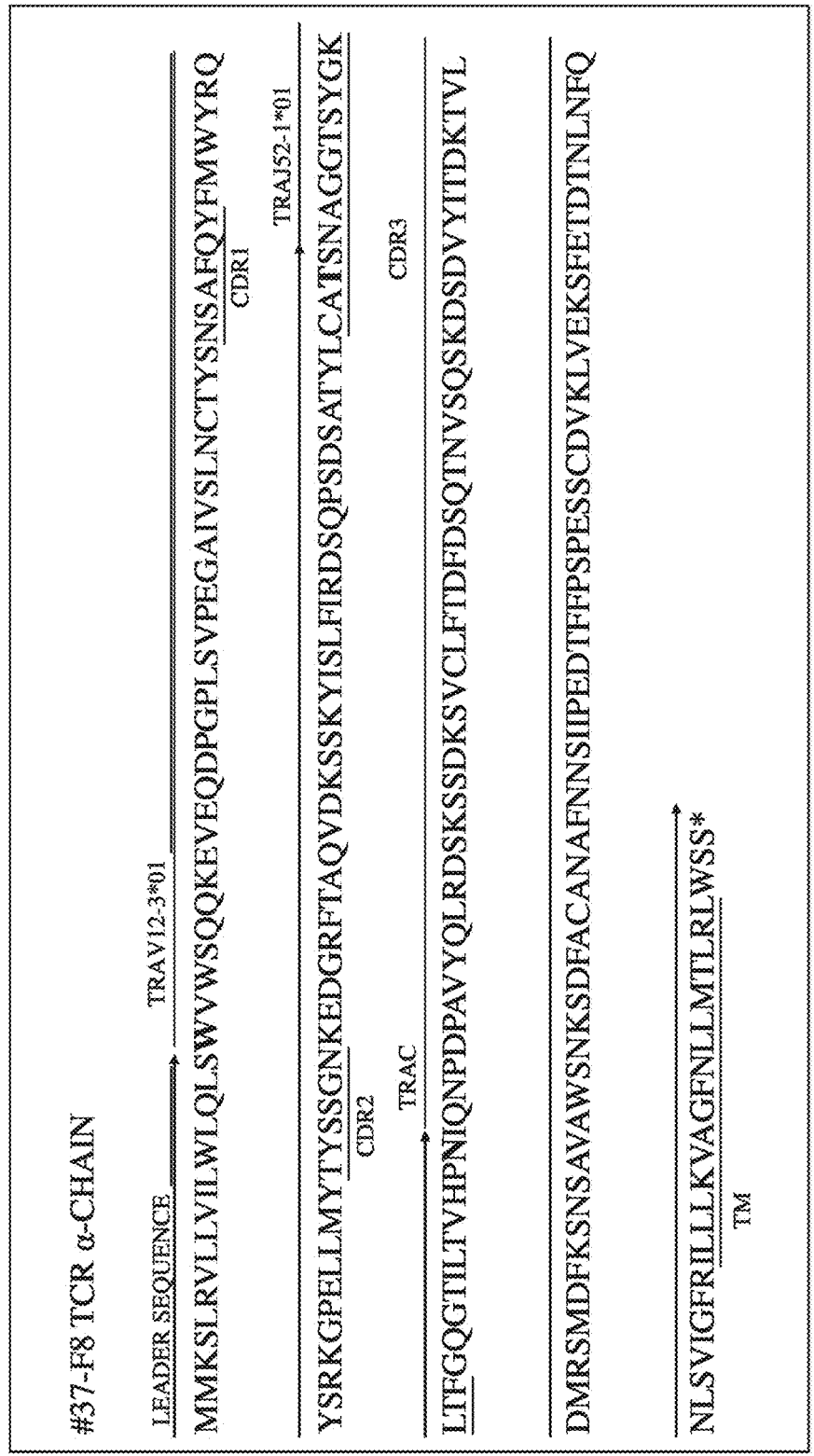
FIG. 14 illustrates a structural feature of α-chain of the TCR specific to HLA-A*24:02 WT1 (SEQ ID NO: 10).

The variable region including these complementarity determining regions may have, for example, substituted, deleted, or added one or more amino acids (for example, several amino acids, three amino acids or less, two amino acids or less) in the amino acid sequence in a region other than the complementarity determining regions. The variable region is preferably a variable region having an amino acid sequence of SEQ ID NO: 4. The TCR α-chain protein of the present invention preferably has an amino acid sequence of SEQ ID NO: 14 (SEQ ID NO: 14 is an amino acid sequence obtained by removing a leader sequence and a TM sequence from the TCR α-chain protein described in FIG. 14).

On the other hand, the TCR β-chain protein constituting TCR complex identified by the present inventors comprises, as complementarity determining regions on a variable region, CDR1 having an amino acid sequence of SEQ ID NO: 5, CDR2 having an amino acid sequence of SEQ ID NO: 6, and CDR3 having an amino acid sequence of SEQ ID NO: 7. Thus, the present invention provides a TCR β-chain protein having amino acid sequences of SEQ ID NOs: 5 to 7. The variable region including these complementarity determining regions may have, for example, substituted, deleted, or added one or more amino acids (for example, several amino acids, three amino acids or less, two amino acids or less) in the amino acid sequence in a region other than the complementarity determining regions. The variable region is preferably a variable region having an amino acid sequence of SEQ ID NO: 8. The TCR β-chain protein of the present invention preferably has an amino acid sequence of SEQ ID NO: 15 (SEQ ID NO: 15 is an amino acid sequence obtained by removing a leader sequence and a TM sequence from the TCR β-chain protein described in FIG. 15).

<Genes, Vector, Transformed Cells>

The present invention also provides an isolated DNA encoding the TCR α-chain protein, and an isolated DNA encoding the TCR β-chain protein. The TCR α-chain protein, the TCR β-chain protein, or the TCR complex comprising these proteins can be expressed in cells by incorporating the DNA(s) into an expression vector, which is then introduced into the cells. The vector used to express these proteins in cells may be a vector described in the present Examples, but is not limited thereto. For example, a vector pIRES (Takara Bio Inc.) capable of translating two genes from a single mRNA via IRES, vectors in MAMMALIAN POWEREXPRESS SYSTEM® (Toyobo Co., Ltd.), and the like can also be used. The vector may be a vector comprising and being capable of expressing any one of the DNA encoding the TCR α-chain protein and the DNA encoding the TCR β-chain protein, or may be a vector comprising and being capable of expressing the two. The cells into which the vector is introduced are not particularly limited, and various cells can be used in accordance with the purpose. The genes can be introduced into cells by methods known to those skilled in the art, such as an electroporation method.

The transformed cells thus prepared can be utilized, for example, as a companion diagnostic agent in performing a peptide vaccination. When a peptide vaccination is performed, what peptide should be used as the vaccine is important diagnostic information. The use of the transformed cells makes it possible to judge whether or not a WT1 peptide restricted to HLA-A*24:02 is presented in the membrane surface of the target cells. For such a purpose, cells capable of producing a cytokine in response to a stimulus, such as Jurkat, HPB-ALL, and HPB-MLT, can be used as the cells used for preparing the transformed cells. This makes it possible to detect the existence of a WT1 peptide restricted to HLA-A*24:02 in the membrane surface of target cells on the basis of cytokine production in the transformed cells (see Example 10). Meanwhile, dendritic cell vaccinations have been performed in which a peptide is bound to dendritic cells separated from a patient and then inoculated into the patient. Actually, the above-described transformed cells can also be utilized as a reagent for checking a peptide presented by a specific HLA on dendritic cells.

Another preferable embodiment of the transformed cell of the present invention is a transformed cell detectable by a molecule multimerized by binding a wildtype WT1 peptide restricted to HLA-A*24:02 and a molecule multimerized by binding a mutant WT1 peptide restricted to HLA-A*24:02.

The "molecule multimerized by binding a wildtype WT1 peptide restricted to HLA-A*24:02" or the "molecule multimerized by binding a mutant WT1 peptide restricted to HLA-A*24:02" can be prepared by the methods described in Science, 1996; 274: 94-96, U.S. Pat. No. 5,635,363, and Japanese Patent No. 3506384. Specifically, HLA-A*24:02, a β2m (β2-microglobulin) recombinant protein, and a chemically synthesized wildtype WT1 peptide or mutant WT1 peptide are associated with each other with stirring in a folding solution to form a complex of HLA-A*24:02, β2m, and the peptide (hereinafter referred to as "monomer"). Subsequently, biotin is bound, by an enzymatic reaction, to an amino acid at a single site on the C-terminus side of HLA-A*24:02 constituting the monomer. The biotinylated monomer is purified by column chromatography, and then caused to react with avidin. Thus, the multimerized molecule can be synthesized. By labeling avidin in advance with a fluorescent substance such as FITC (fluorescein isothiocyanate), PE (Phycoerythrin), or APC (allophycocyanin), the antigen specific T cells can be detected using a flow cytometer or a fluorescence microscope.

An example of a product of the "molecule multimerized by binding a wildtype WT1 peptide restricted to HLA-A*24:02" includes T-Select HLA-A*24:02 WT1 (wildtype) Tetramer-CMTWNQMNL-PE Kit to be prepared at the time of use (MBL Co., Ltd.; produced on order). Examples of a product of the "molecule multimerized by binding a mutant WT1 peptide restricted to HLA-A*24:02" include T-Select HLA-A*24:02 WT1 (mutant) Tetramer-CYTWNQMNL-PE and T-Select HLA-A*24:02 WT1 (mutant) Tetramer-CYTWNQMNL-APC (MBL Co., Ltd.; the product codes are respectively TS-M014-1 and TS-M014-2).

Examples of cells used for preparing such transformed cells include Sup-T1 deficient in TCR α-chain and J.RT3-T3.5 deficient in TCR β-chain, a variant of Jurkat derived from human leukemia. A transformed cell line SK37 prepared using these cells (see Example 6) is a cell line having an infinite proliferative potential but no infectious concern. Further, since no complicated special culture method is required for the proliferation, the cell line can also be distributed as positive control cells of an HLA-A*24:02 WT1 tetramer reagent. The experimenter can check a reactivity of an HLA-A*24:02 WT1 tetramer reagent any time by using SK37 as the positive control cells. This presumably results in great increases in the accuracy and the reliability of data to be obtained from clinical specimens. Moreover, the cell line is advantageous also in setting loading conditions in flow cytometry. When distributed, SK37 can also be stored and transported utilizing normal liquid nitrogen or dry ice, and can also be stored and transported under cold conditions by diluting SK37 in an appropriate solution such as one used for Immuno-TROL™ Cells (Beckman Coulter, Inc.), which are human whole blood control cells for flow cytometry. Furthermore, it is also possible to improve the advantage by lyophilization (U.S. Pat. No. 5,861,311).

Another preferable embodiment of the transformed cell of the present invention is a transformed cell prepared using a lymphocyte. For example, the gene is introduced into a sample of human peripheral blood lymphocytes, and the resultant is returned into the body for cancer treatment. Thus, the present invention also provides a pharmaceutical composition for treating a WT1 positive cancer, the pharmaceutical composition comprising the transformed cell of the present invention as an active ingredient.

Examples of the WT1 positive cancer targeted by such a treatment include, but are not limited to, leukemia and solid cancers such as brain tumors, pancreatic cancer, kidney cancer, mesothelioma, stomach cancer, colorectal cancer, lung cancer, breast cancer, germ cell cancer, liver cancer, skin cancer, bladder cancer, prostate cancer, uterine cancer, and cervical cancer, ovarian cancer, and others (see Japanese Patent No. 3819930).

Note that the cytotoxic activity of the prepared cells can be measured by a chromium release assay using target cells that are labeled utilizing a radioactive isotope $^{51}Cr$ (see Example 2). In addition, the cytotoxic activity can also be measured, for example, using IMMUNOCYTO Cytotoxicity Detection Kit (MBL Co., Ltd.) with which target cells are labeled with CFSE (Dojindo Laboratories), Cytotoxicity Detection Kit (Roche Diagnostics) with which LDH (lactate dehydrogenase) released from target cells is measured, or the like.

<Antibodies>

Moreover, the present invention provides an isolated antibody capable of specifically binding to the TCR α-chain protein, an isolated antibody capable of specifically binding to the TCR β-chain protein, and an isolated antibody capable of specifically binding to the TCR complex comprising these proteins.

The use of these antibodies makes it possible to specifically detect the TCR of the present invention expressed on the cell surface. The antibody of the present invention can be used, for example, for testing of the transformed cell and the pharmaceutical composition of the present invention. Moreover, the antibody of the present invention can also be used for isolation of the transformed cell and the pharmaceutical composition of the present invention in the production processes thereof so as to improve the purities. Furthermore, after the pharmaceutical composition is administered to a patient, the antibody of the present invention can also be used to quantify the active ingredient in peripheral blood of the patient.

The antibody of the present invention is preferably a monoclonal antibody. A typical example of the method for producing the monoclonal antibody is a method by Kohler and Milstein (Kohler & Milstein, Nature, 256: 495 (1975)). Antibody-producing cells used in cell fusion process of this method are spleen cells, lymph node cells, peripheral blood leukocytes, and the like of an animal (for example, mouse, rat, hamster, rabbit, monkey, goat) immunized with the antigenic TCR α-chain protein or TCR β-chain protein. It is also possible to use antibody-producing cells obtained by causing the antigen to act, in a medium, on the above-described types of cells, lymphocytes, or the like, which have been isolated from non-immunized animals in advance. As myeloma cells, known various cell lines can be used. Hybridomas can be produced, for example, by cell fusion between mouse myeloma cells and spleen cells obtained from a mouse immunized with the antigen. By the subsequent screening, a hybridoma which produces a monoclonal antibody against the antigen can be obtained. The monoclonal antibody against the antigen can be obtained by culturing the hybridoma, or from an ascites of a mammal to which the hybridoma is administered.

The antibody can also be produced as a recombinant antibody. Specifically, an isolated DNA encoding the antibody is cloned from hybridomas, B cells, or the like. The cloned DNA is incorporated into an appropriate vector, which is introduced into host cells (for example, a mammalian cell line, *Escherichia coli*, yeast cells, insect cells, plant cells, or the like) for the production (for example, Antibody Production: Essential Techniques, 1997 WILEY, Monoclonal Antibodies, 2000 OXFORD UNIVERSITY PRESS, Eur. J. Biochem. 192: 767-775 (1990)). When a transgenic animal (cattle, goat, sheep, pig, or the like) incorporating the antibody gene is produced using a transgenic animal production technique, a large amount of monoclonal antibodies derived from the antibody gene can also be obtained from milk of the transgenic animal.

The antibody of the present invention may be labeled for detection of the TCR. As the label, it is possible to use, for example, a radioactive substance, a fluorescent dye, a chemiluminescent substance, an enzyme, a coenzyme, or the like. Moreover, for the isolation of the TCR, a tag may be added. As a tag, it is possible to use, for example, magnetic beads, biotin, avidin, or the like.

<TCR Multimer>

The present invention also provides a molecule multimerized by binding the TCR complex. The molecule can be prepared, for example, as follows. A DNA encoding an extracellular region of the TCR is incorporated into an expression vector, TCR α-chain and β-chain recombinant proteins are artificially prepared, and the C-terminus of the TCR α-chain or β-chain is biotinylated utilizing an enzymatic reaction. The biotinylated TCR complex is purified by column chromatography, and then caused to react with avidin. Thus, a multimerized molecule can be prepared. By labeling avidin in advance with a fluorescent substance such as FITC (fluorescein isothiocyanate), PE (Phycoerythrin), or APC (allophycocyanin), cells expressing a specific MHC/peptide complex can be detected using a flow cytometer or a fluorescence microscope. A scTCR can be prepared by linking extracellular regions of TCR α-chain and β-chain using a short peptide linker, and expressing them as a single protein. As in the case of TCR tetramers, multimerization is also possible by biotinylating the C-terminus side. Moreover, multimerization is possible through the incorporation into a variable region of IgG.

The molecule thus prepared can be utilized, like the transformed cell of the present invention, as a companion diagnostic agent in performing a peptide vaccination, or reagent for checking a peptide presented by a specific HLA on dendritic cells when a dendritic cell vaccination is performed. Further, the molecule can also be utilized as a tool in drug delivery system (DDS) by binding the molecule to a radioactive isotope or an anticancer drug for the purpose of cancer treatment, and. Thus, the present invention also provides a drug for detecting or capturing any one of a wildtype WT1 peptide restricted to HLA-A*24:02 and a mutant WT1 peptide restricted to HLA-A*24:02, the drug comprising the molecule of the present invention.

<Detection Kit>

The present invention also provides a kit for detecting any one of a wildtype WT1 peptide restricted to HLA-A*24:02 and a mutant WT1 peptide restricted to HLA-A*24:02, the kit comprising at least one component of (a) to (h) below:

(a) the TCR α-chain protein of the present invention;

(b) the TCR β-chain protein of the present invention;

(c) the TCR complex of the present invention;

(d) the DNA encoding any one of the protein (a) and the protein (b);

(e) a vector comprising and being capable of expressing the DNA (d);

(f) a transformed cell comprising the DNA (d);

(g) an isolated antibody capable of specifically binding to one of the protein (a), the protein (b), and the complex (c); and (h) a molecule multimerized by binding the complex (c).

Here, the "wildtype WT1 peptide restricted to HLA-A*24:02" and the "mutant WT1 peptide restricted to HLA-A*24:02" mean to include, as described above, both a case where these peptides exist on the cell surface, and a case where the peptides exist as isolated or purified molecules (for example, molecules having these peptides restricted to a multimerized TCR complex). The kit of the present invention may further comprise an instruction of the kit.

<Quality Management of WT1 Multimer>

The present invention also provides a quality management method for any one of a molecule multimerized by binding a wildtype WT1 peptide restricted to HLA-A*24:02 and a molecule multimerized by binding a mutant WT1 peptide restricted to HLA-A*24:02, the method comprising a step of checking a reactivity between the molecule and the transformed cell of the present invention. In the quality management method of the present invention, the reactivity can be checked, for example, by methods described in the present Examples 8 and 9. As a result, when the reactivity is retained, the quality of the molecule can be evaluated as being retained. On the other hand, when the reactivity is lowered, the quality of the molecule can be evaluated as being lowered. Note that whether the reactivity is retained or not can be judged, for example, based on whether the positive ratio is retained or not and/or MFI (mean fluorescence intensity) is retained or not. Further, a defect in the quality is inferred from a decrease in any one of the indexes, and an improvement measure can be taken.

EXAMPLES

Hereinafter, the present invention will be described more specifically based on Examples. However, the present invention is not limited to the following Examples.

[Example 1] Induction of HLA-A*24:02 WT1 Peptide Specific CTL Lines, and Culturing for Proliferation Using various cancer antigen-derived peptides, the present inventors repeatedly examined and modified a MLPC (mixed lymphocyte-peptide cultures) process, by which a cancer antigen specific CTL was efficiently cultured to proliferate under limiting dilution conditions, with reference to the paper by Karaniks et al. reported in 2003 (J. Immunol., 2003; 171: 4898-4904). The inventors utilized the MLPC method as an induction method for cancer antigen specific CTL. The present inventors have empirically found out that the ratio of cancer antigen specific CTL present was less than 1 relative to $1 \times 10^7$ of peripheral blood mononuclear cells (PBMCs) from healthy subjects. For example, when $5 \times 10^5$ PBMCs are added to each well of a 96-well plate to induce CTLs, specific CTL induction is observed in at most 5 wells among the 96 wells. Thus, it can be said that this condition is limiting dilution conditions. The MLPC method is a method for merely adding an antigenic peptide to PBMCs followed by culturing, by which memory T cells or memory/effector T cells existing in the body of a blood donor are presumably stimulated and proliferated. Accordingly, it is believed that there is a low risk of artificial stimulation and proliferation of T cells due to artificial priming of naive T cells as assumed in a case of utilizing antigen-presenting cells prepared in vitro. The present inventors induced HLA-A*24:02 WT1 peptide specific CTL lines, as follows, under the limiting dilution conditions that the present inventors had empirically found out.

Human PBMCs already known to have HLA-A*24:02 in an amount equivalent to those in three people were purchased from Cellular Technology Limited. The concentration of the PBMCs was adjusted to $1 \times 10^6$ to $5 \times 10^6$/mL with a CTL medium (5% human AB serum/100 U/mL Penicillin/100 µg/mL Streptomycin/1×GlutaMAX/55 µM 2-Mercaptoethanol/25 mM HEPES/PRMI-1640). To the resultant, HLA-A*24:02 WT1 mutant peptide (CYTWNQMNL, MBL Co., Ltd.) was added to make the final concentration 10 µg/mL. After thorough stirring, 100 µL of the resultant was dispensed into each well of 96-well U-bottom plates. Then, the cells were cultured in a 5% $CO_2$ incubator at 37° C. for 48 hours. After 48 hours, 100 µL of a CTL medium containing 100 U/mL of IL-2 (Shionogi & Co., Ltd.) was added thereto, and the culturing was continued. The CTL medium was replaced by removing approximately a half of the medium by suction and adding a CTL medium supplemented with 50 U/mL of IL-2, while the culture state was being observed. In the first one week, the medium was replaced once, and after one week elapsed, the medium was replaced every 2 to 3 days.

At 10 to 14 days after the culturing was started, 70 µL of the cell suspension was collected from each well, and stained with an HLA-A*24:02 WT1 (wildtype) tetramer CMTWNQMNL-PE (hereinafter abbreviated as "HLA-A*24:02 WT1 (wildtype) tetramer reagent," MBL Co., Ltd.) and an HLA-A*24:02 WT1 (mutant) tetramer CYTWNQMNL-PE (hereinafter abbreviated as "HLA-A*24:02 WT1 (mutant) tetramer reagent," MBL Co., Ltd.). The staining procedure is as follows.

To the collected cell suspension, an FCM buffer [2% FBS (fetal bovine serum)/0.05% $NaN_3$/PBS] was added and centrifuged at 400×g for 5 minutes. After the supernatant was removed by suction, an appropriate amount of an FCM buffer was again added and centrifuged at 400×g for 5 minutes. Then, the supernatant was removed by suction. After 20 µL of an FCM buffer and 10 µL of Clear Back Human FcR blocking reagent (MBL Co., Ltd.) were added and thoroughly stirred, the resultant was left standing at room temperature for 5 minutes. After 10 µL of the HLA-A*24:02 WT1 (mutant) tetramer reagent was added and gently stirred, the mixture was allowed to react in a cold chamber at 2 to 8° C. for 30 minutes. To this, 10 µL of CD8 (clone T8)-FITC (Beckman Coulter, Inc.) was added, and allowed to react in the cold chamber for 20 minutes. An appropriate amount of an FCM buffer was added thereto and centrifuged at 400×g for 5 minutes. The supernatant was carefully discarded. To the resultant, 400 µL of an FCM buffer supplemented with 7-AAD (Beckman Coulter, Inc.) by 1% was added to suspend the cells therein. The cells were loaded into a flow cytometer (FACSCalibur, BD biosciences) for analysis. The analysis data was analyzed using CellQuest software (BD biosciences) or FlowJo (Tree Star Inc.). From the result, wells were selected, in which cell populations stained with the HLA-A*24:02 WT1 (mutant) tetramer reagent were detected. Furthermore, 35 µL of each of the cell suspensions was collected, and a reactivity with the HLA-A*24:02 WT1 (wildtype) tetramer reagent was similarly checked. As a control of the MHC tetramer reagents, HLA-A*24:02 HIV env tetramer RYLRDQQLL-PE (MBL Co., Ltd.) was used for staining. As a result, it was verified that the staining was not non-specific. This reagent is synthesized using HLA-A*24:02 as MHC and a peptide derived from an HIV (human immunodeficiency virus) envelope as the antigenic peptide, and is capable of detecting and quantifying a CTL population specific to the reagent. The reagent is often utilized as a negative control of a MHC tetramer reagent because the HIV morbidity rate is low in Japan. Additionally, since the CTL existing frequency is basically low, when determining whether or not MHC-tetramer reagent positive cells exist, it is very important to use such a negative control MHC tetramer reagent as a control. As a result of the staining test, cell populations were obtained, which exhibited a reactivity to both of the HLA-A*24:02 WT1 (wildtype) tetramer reagent and the HLA-A*24:02 WT1 (mutant) tetramer reagent in seven wells.

Using antigen-presenting cells pulsed with a WT1 (mutant) peptide, these cell populations were restimulated at intervals of approximately 2 to 3 weeks, and the culturing was continued for approximately 2 months. The antigen-presenting cells used were mainly lymphoblastoid cell lines (LCL) obtained by immortalizing human B cells with an EB virus. Nevertheless, it is also possible to use activated T cells, which are activated with a T cells stimulator such as an anti-CD3 antibody, PHA (phytohemagglutinin), or IL-2. It is important that these antigen-presenting cells express HLA-A*24:02 on the cell surface, and whether HLA-A*24:02 is expressed or not can be checked by flow cytometry using, for example, an anti-HLA-A24 antibody (MBL Co., Ltd.) or the like. Alternatively, instead of using the antigen-presenting cells, it is also possible to employ, for example, a method in which a proliferative stimulus is directly added to CTL by utilizing the CTL-proliferating action of an anti-CD137 antibody (WO2008/023786).

The peptide pulsing was performed as follows. HLA-A*24:02 positive antigen-presenting cells were washed with 2% FBS/PBS once, and then suspended in 1 mL of a peptide-pulsing medium [0.1% HSA (human serum albumin)/55 µM 2-Mercaptoethanol/RPMI 1640] or AIM-V medium (Life Technologies Corporation), and the WT1 (mutant) peptide was added so that the final concentration was 10 µg/mL. After thorough stirring, the resultant was incubated at room temperature for 1 hour while gently mixed at intervals of approximately 15 minute. Presumably, this operation causes the WT1 (mutant) peptide to bind to HLA molecules on the antigen-presenting cells. Subsequently, an appropriate amount of the peptide-pulsing medium was added, thoroughly stirred, and then centrifuged at 400×g for 5 minutes. After the centrifugation, the supernatant was carefully discarded. In order to completely remove an excessive amount of the peptide, this washing treatment was further performed twice. Thereafter, the resultant was resuspended in an appropriate amount of a CTL medium, and the number of the cells was counted. It is important to make these antigen-presenting cells have no proliferative potential by X-ray irradiation, mitomycin treatment, or the like. The X-ray irradiation may be conducted simultaneously with the incubation at room temperature for 1 hour after the peptide is mixed with the antigen-presenting cells. The mitomycin treatment is desirably performed before the peptide pulsing. The amount of the peptide-pulsed antigen-presenting cells added was within a range from ⅒ to equal amount corresponding to the cell count of the cell populations exhibiting the reactivity to the HLA-A*24:02 WT1 tetramer reagents.

There were two CTL cell populations (37F8 and 32F3) exhibiting the reactivity to both of the HLA-A*24:02 WT1 (wildtype) tetramer reagent and the HLA-A*24:02 WT1 (mutant) tetramer reagent and successfully cultured for 2 months.

FIG. 1 illustrates the reactivity of the two CTL populations (37F8 and 32F3) to the MHC tetramer reagents. FIG. 1A shows dot plot distribution charts in which the X axis represents the staining intensity (log scale) of an FITC-labeled anti-CD8 antibody, and the Y axis represents the staining intensity (log scale) of the PE-labeled MHC tetramer reagents. The upper portions of the dot plots indicate the type of MHC tetramer reagent used. The upper right quadrant of each dot plot shows an existing ratio (%) of CTLs positive for the anti-CD8 antibody and positive for the corresponding MHC tetramer reagent in viable cells. The upper charts show the result of 37F8, and the lower charts show the result of 32F3.

A ratio of the CTLs positive for the anti-CD8 antibody and specific to the HLA-A*24:02 WT1 tetramer reagents in the cell population was 97% for 37F8 and 35% to 39% for 32F3. Since the positive ratio for the HLA-A*24:02 HIV env tetramer reagent was 0%, the cell populations positive for the anti-CD8 antibody and positive for the HLA-A*24:02 WT1 tetramer reagents were considered to be specific CTL populations.

Figure 1B:
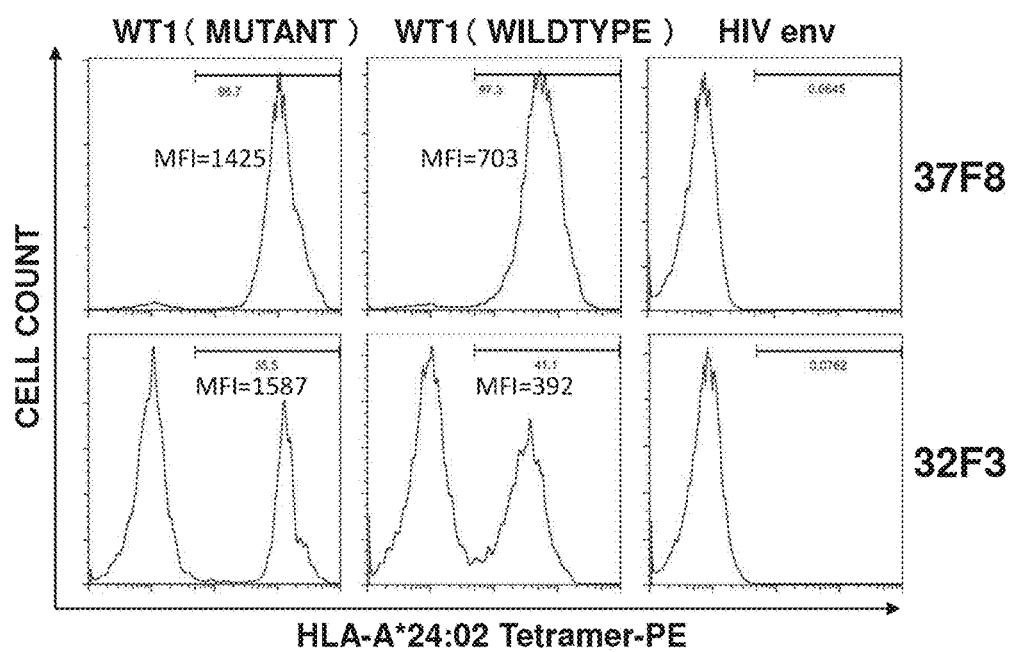
FIG. 1B shows histogram distribution charts for illustrating the reactivity of the two CTL populations (37F8 and 32F3) to the MHC tetramer reagents. In the charts, the X axis represents the staining intensity (log scale) of the PE-labeled MHC tetramer reagents, and the Y axis represents the cell count. The upper portions of the histogram distribution charts indicate the type of MHC tetramer reagent used. The upper charts show the result of 37F8, and the lower charts show the result of 32F3. The numerical value under the horizontal line in each histogram distribution chart indicates the position of the marker where MFI (mean fluorescence intensity) is calculated.

FIG. 1B shows histogram distribution charts in which the X axis represents the staining intensity (log scale) of the PE-labeled MHC tetramer reagents, and the Y axis represents the cell count. The upper portions of the histogram distribution charts indicate the type of MHC tetramer reagent used. The upper charts show the result of 37F8, and the lower charts show the result of 32F3. The numerical value under the horizontal line in each histogram distribution chart indicates the position of the marker where MFI (mean fluorescence intensity) was calculated. MFI is information indicative of the binding strength between a PE-labeled MHC tetramer reagent and TCR expressed on the CTL cell surface. The higher the MFI, presumably the higher the binding strength or the larger the number of TCR molecules expressed on one cell surface.

The MFI of the population positive for the PE-labeled MHC tetramer reagent and stained with the HLA-A*24:02 WT1 (mutant) tetramer reagent was 1,425 for 37F8 and 1,587 for 32F3. One the other hand, when the population was stained with the HLA-A*24:02 WT1 (wildtype) tetramer reagent, the MFI was 703 for 37F8 and 392 for 32F3.

In 37F8, a ratio of the MFI between the HLA-A*24:02 WT1 (wildtype) tetramer reagent and the HLA-A*24:02 WT1 (mutant) tetramer reagent was approximately 2. Meanwhile, in the case of 32F3, the ratio was 4. In detecting the HLA-A*24:02 WT1 (wildtype) tetramer reagent, the higher the MFI, the more clearly positive and negative are distinguished from each other. The ratio of the cells positive for the HLA-A*24:02 WT1 tetramer reagents in the entire viable cell population is high. From these facts, the subsequent analyses were performed using 37F8.

[Example 2] Checking Cytotoxic Activity of 37F8

It was revealed that cells having TCRs capable of reacting with the HLA-A*24:02 WT1 tetramer reagents existed at a ratio of 97% in 37F8. Meanwhile, the HLA-A*24:02 WT1 tetramer reagents are complexes each constituted of three components: artificially synthesized HLA-A*24:02, β2-microglobulin, and a WT1 peptide. Accordingly, it is necessary to check whether the TCRs are capable of recognizing the three-component complexes expressed on the actual cell surface. Further, whether or not CTLs having the TCRs are activated by binding between the TCRs and the three-component complexes and can demonstrate a cytotoxic activity on cells expressing the three-component complexes is important to infer whether lymphocytes having α-chain and β-chain of the 37F8-derived TCR artificially introduced and expressed function in vivo. For this reason, measured was the cytotoxic activity of the CTL cell population (37F8) specific to HLA-A*24:02-restricted WT1 peptides and detectable as the cell population positive for the HLA-A*24: 02 WT1 tetramer reagents.

The cytotoxic activity was checked according to the conventional method using the 37F8 cells as effector cells and HLA-A*24:02 positive LCL and HLA-A*24:02 negative LCL as target cells.

The specific experimental method will be described below. In 100 µL of a medium, 3.7 MBq $^{51}$Cr (Na$_2$CrO$_4$, Japan Radioisotope Association) was added to the HLA-A*24:02 positive or negative LCL and labeled in a 5% CO$_2$ incubator at 37° C. for 1 hour. After washed with 2% FBS/PBS once, the resultant was suspended in 1 mL of a peptide-pulsing medium. The WT1 (wildtype) peptide or the WT1 (mutant) peptide was added so that the final concentration was 1 µg/mL. After thorough stirring, the resultant was incubated at room temperature for 1 hour. An excessive amount of a peptide-pulsing medium was added thereto, thoroughly stirred, and then centrifuged at 400×g for 5 minutes. After the centrifugation, the supernatant was carefully discarded. In order to remove an excessive amount of the peptide, this washing treatment was further performed twice. Thereafter, the resultant was resuspended in an appropriate amount of a CTL medium, and the number of the cells was counted. To each well of 96-well V-bottom plates, 2,000 of the target cells and 6,000 to 200,000 of the effector cells were added, and cultured in a 5% CO$_2$ incubator at 37° C. for 4 hours. After centrifugation at 400×g for 5 minutes, 100

μL of the supernatant was collected from the 96-well V-bottom plates, and the radioactivity was measured with a gamma counter.

The cytotoxic activity (%) was calculated according to the following equation: [sample release (cpm)−spontaneous release (cpm)]/[maximum release (cpm)−spontaneous release (cpm)]×100. The value of the maximum release (cpm) was obtained by adding 2% Triton X-100 to a target cell suspension, and the spontaneous release (cpm) was a measured value of a suspension containing only the target cells. The value of the cytotoxic activity (%) was expressed as the mean of three samples±standard error, and a t-test was conducted for the statistical processing between two groups. The result would be statistically significant with a critical p value being <0.05.

Figure 2:
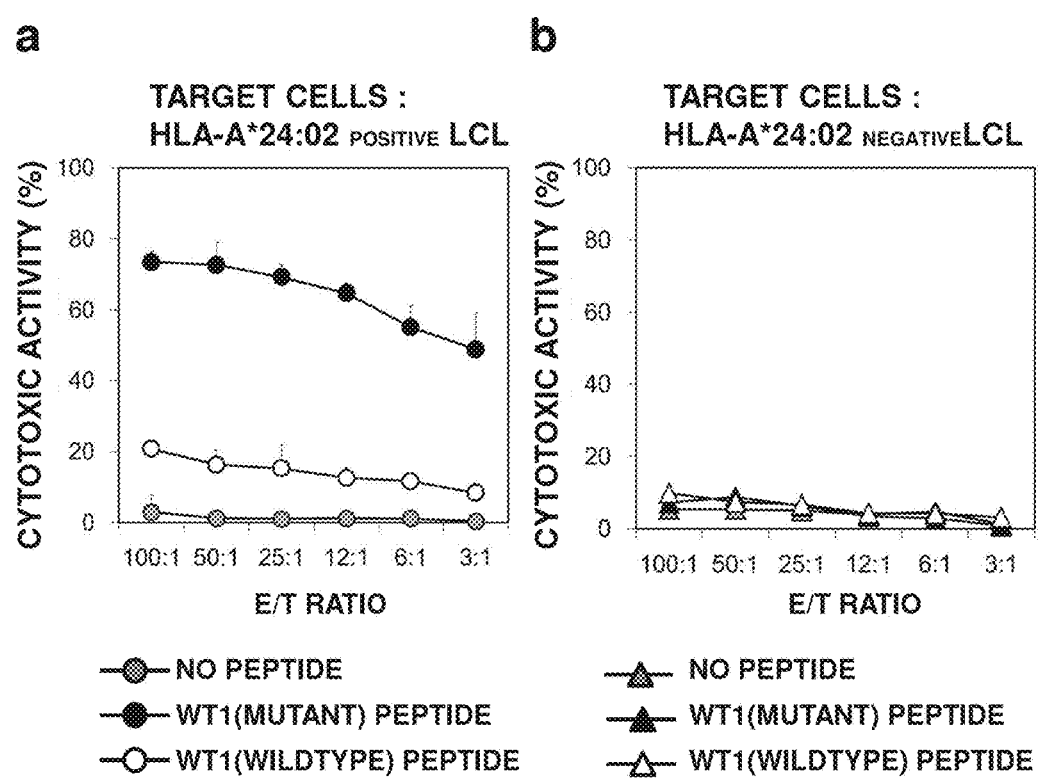
FIG. 2 shows graphs for illustrating the result of detecting the cytotoxic activity of the CTL cell population 37F8. The X axis represents a ratio of the number of effector cells to the number of target cells (E/T ratio), and the Y axis represents the cytotoxic activity (%). (a) shows the result obtained when HLA-A*24:02 positive LCL (Blymphoblast: lymphoblastoid cell line) was used as the target cells, and (b) shows the result obtained when HLA-A*24:02 negative LCL was used as the target cells.

FIG. 2 shows the result. The X axis represents a ratio of the number of the effector cells to the number of the target cells (E/T ratio), and the Y axis represents the cytotoxic activity (%). Part a of FIG. 2 shows the result obtained when the HLA-A*24:02 positive LCL was used as the target cells, and Part b of FIG. 2 shows the result obtained when the HLA-A*24:02 negative LCL was used as the target cells. The cytotoxic activity of 73% at maximum was observed on the LCL pulsed with the WT1 (mutant) peptide, and the cytotoxic activity of 20% was observed on the LCL pulsed with the WT1 (wildtype) peptide. On the other hand, the cytotoxic activity was hardly detected in the LCL not pulsed with any peptide and in the HLA-A*24:02 negative LCL.

[Example 3] Repertoire Analysis on TCR of WT1 Specific CTL Cell Population 37F8

The present inventors thought that information obtainable before genetic information extraction should be obtained in order to avoid unpredictable mutation insertion attributable to PCR repeatedly carried out in the process of obtaining genes. For this purpose, a kit (IOTest beta Mark TCR Vβ Repertoire Kit, Beckman Coulter, Inc.) was used, which was capable of repertoire analysis on 24 types of a Vβ region of TCR β-chain by flow cytometry using antibodies capable of specifically recognizing the Vβ region. The kit includes the following 24 antibodies specific to the TCR Vβ region: Vβ1, Vβ2, Vβ3, Vβ4, Vβ5.1, Vβ5.2, Vβ5.3, Vβ7.1, Vβ7.2, Vβ8, Vβ9, Vβ11, Vβ12, Vβ13.1, Vβ13.2, Vβ13.6, Vβ14, Vβ16, Vβ17, Vβ18, Vβ20, Vβ21.3, Vβ22, and Vβ23. This kit is capable of detecting approximately 70% of the TCR β-chain Vβ region, and identifying information only on the TCR β-chain Vβ region.

Figure 3:
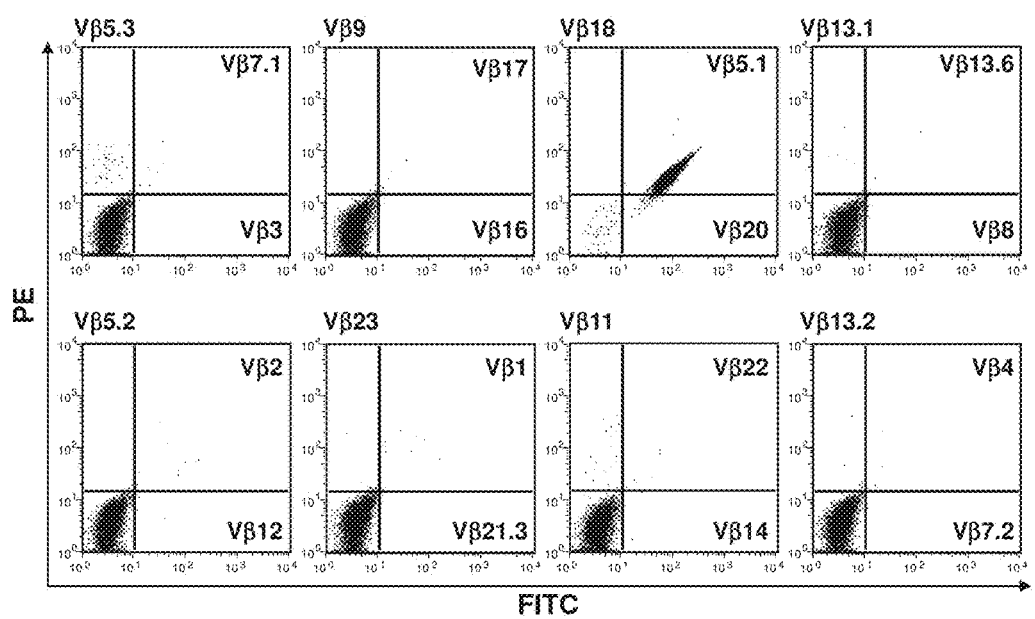
FIG. 3 shows dot plot distribution charts for illustrating the result of a stain analysis on a TCR Vβ region of the CTL cell population 37F8.

FIG. 3 shows the result of the stain analysis performed on the CTL cell population 37F8 specific to the HLA-A*24:02 WT1 peptides according to the operation procedure of the data sheet. The kit includes eight staining reagents, and staining 37F8 with the eight reagents enables analysis on the 24 types of Vβ region. One reagent contains an FITC-labeled anti-Vβ antibody, a PE-labeled anti-Vβ antibody, and an anti-Vβ antibody labeled with both of PE and FITC. FIG. 3 shows dot plot distribution charts in which the X axis represents the fluorescence intensity (log scale) of the FITC-labeled anti-Vβ antibody, and the Y axis represents the fluorescence intensity (log scale) of the PE-labeled anti-Vβ antibody. In each dot plot distribution chart, the lower left quadrant region illustrates a cell population not stained with any antibody, the upper left quadrant region illustrates a cell population stained with the PE-labeled anti-Vβ antibody, the upper right quadrant region illustrates a cell population stained with the anti-Vβ antibody labeled with both of PE and FITC, and the lower right quadrant region illustrates a cell population stained with the FITC-labeled anti-Vβ antibody. The subgroup names of the Vβ regions specifically stained with the anti-Vβ antibodies are noted in the charts. The result revealed that almost all the cells included in the 37F8 cell population had Vβ5.1, and that cells having Vβ5.3 and Vβ11 were included in quite small amounts. Since the existing ratio of the cells positive for the anti-CD8 antibody and positive for the HLA-A*24:02 WT1 tetramer reagents in 37F8 is 97% as shown in FIG. 1A also, it is suggested that the TCR β-chain Vβ region specific to the HLA-A*24:02 WT1 peptides included in 37F8 belongs to the subgroup Vβ5.1.

[Example 4] Cloning of TCR Genes Derived from WT1 Specific CTL Cell Population 37F8

—Isolation of HLA-A*24:02 WT1 Tetramer Reagent Positive Cells from 37F8—

As shown in FIG. 1A, approximately 97% of the cell population 37F8 exhibited the reactivity to the HLA-A*24:02 WT1 tetramer reagents. As a result of the repertoire analysis on the TCR Vβ-chain shown in FIG. 3, a great number of cells had Vβ5.1, but cells having Vβ5.3 and Vβ11 were included in quite small amounts. Because of the existing ratios, the cells having Vβ5.3 and Vβ11 are not apparently a cell population having the target TCR. If genetic information from these cells is mixed, this poses a considerable obstacle in determining a correct combination of TCR α-chain and β-chain. Particularly, the gene amplification efficiency of PCR is greatly influenced, depending on the primer design. A PCR product having a high amplification efficiency does not necessarily mean to reflect the cDNA level in a template. The design flexibility for a primer designed to obtain the full-length TCR gene, which is particularly rich in diversity, is significantly low in comparison with the design flexibility for a primer used for normal quantitative PCR. For this reason, approximately 3% of the cell population included in 37F8 and not reacting with the HLA-A*24:02 WT1 tetramer reagents was eliminated before PCR.

First, the 37F8 cell suspension was collected and centrifuged at 400×g for 5 minutes. After the supernatant was removed by suction, an appropriate amount of an FCM buffer was added and centrifuged at 400×g for 5 minutes. Then, the supernatant was removed by suction. After 20 μL of an FCM buffer and 10 μL of Clear Back Human FcR blocking reagent were added and thoroughly stirred, the mixture was allowed to react at room temperature for minutes. After 10 μL of HLA-A*24:02 WT1 (mutant) tetramer CYTWNQMNL-PE was added and gently stirred, the mixture was allowed to react at 4° C. for 15 minutes. To this, 10 μL of CD8 (clone T8)-FITC was added, and allowed to react at 4° C. for 15 minutes. An appropriate amount of an FCM buffer was added thereto and centrifuged at 400×g for 5 minutes. The supernatant was carefully discarded. To the resultant, anti-PE microbeads (Miltenyi Biotec) were added and allowed to react at 4° C. for 15 minutes. The anti-PE microbeads are magnetic beads conjugated with a monoclonal antibody against PE (Phycoerythrin) that is a fluorescent label of a MHC tetramer reagent. Accordingly, the anti-PE microbeads can efficiently separate and concentrate the cell population stained with the MHC tetramer reagent. The cells were separated using an automated magnetic separator autoMACS® (Miltenyi Biotec). Some of a flow-through cell population and a cell population collected at a positive fraction were immediately analyzed with a flow cytometer.

Figure 4:
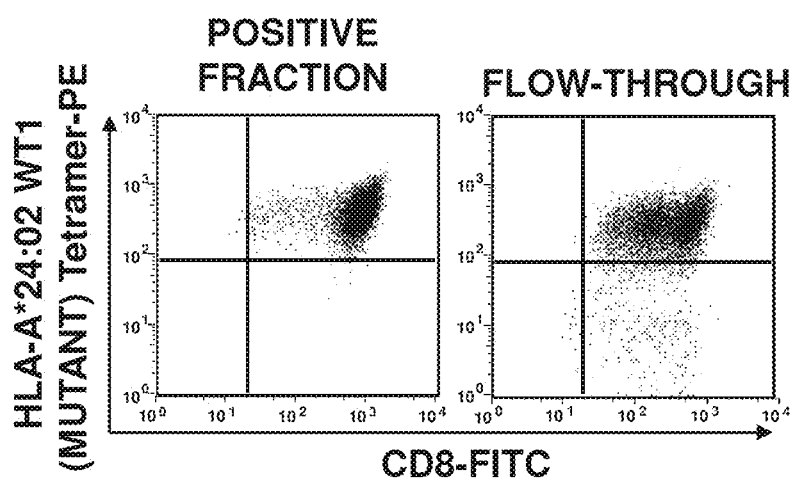
FIG. 4 shows dot plot charts for illustrating the result of detecting the reactivity of the CTL cell population 37F8 to the HLA-A*24:02 WT1 tetramer reagent. The positive fraction is a cell population retained on the magnetic column, and the flow-through is a cell population not retained on the magnetic column. The X axis represents the staining intensity (log scale) of the FITC-labeled anti-CD8 antibody, and the Y axis represents the staining intensity (log scale) of the PE-labeled MHC tetramer reagent. In each dot plot, the cell populations in the upper left and the upper right quadrants are cell populations positive for the MHC tetramer reagent, and the cell populations in the lower left and the lower right quadrants are cell populations negative for the MHC tetramer reagent.

FIG. 4 shows the result. At the positive fraction, the cell population retained on the magnetic column was concentrated. The flow-through is the cell population not retained on the magnetic column. The X axis represents the staining intensity (log scale) of the FITC-labeled anti-CD8 antibody, and the Y axis represents the staining intensity (log scale) of the PE-labeled MHC tetramer reagent. In each dot plot, the cell populations in the upper left and the upper right quadrants are cell populations positive for the MHC tetramer reagent, and the cell populations in the lower left and the lower right quadrants are cell populations negative for the MHC tetramer reagent. It was revealed that the cell population negative for the HLA-A*24:02 WT1 (mutant) tetramer CYTWNQMNL-PE existed in the flow-through, but hardly existed in the positive fraction. The cell population in the positive fraction was collected and cryopreserved.

—Cloning of TCR Gene—

The present inventors comprehensively analyzed the TCR genetic information registered in IMGT®, and designed multiple primers so as to clone all the full-lengths of TCR α-chain and β-chain. An advantage of this method is that the full-length sequence can be obtained in a single PCR. In this method, it is not necessary to design a primer according to the DNA sequence information obtained based on a PCR product; hence, the possibility that a mutation is included is suppressed to the minimum. Nevertheless, the number of primer combinations is enormous, and the number of times the PCR tested using a few cDNAs is limited. For this reason, the following design was made. Specifically, primer mixes are prepared from a mixture of 10 or 11 primers that have been confirmed not to inhibit the PCR reactions from each other. Then, PCR is carried out using the primer mixes. Using all the combinations of the primer mixes from which gene products are obtained, PCR is carried out to thus obtain the full-length sequence. The combinations of the primer mixes and the PCR reaction temperature condition were set, using a cDNA prepared from three cell groups: Jurkat cells whose TCR repertoire had been reported already, untreated human PBMCs, and T cells expressing a specific Vβ-chain. The T cells expressing a specific Vβ-chain were prepared from human PBMCs using the Vβ-chain specific antibody, and separated and concentrated with an automated magnetic separator.

Figure 5:
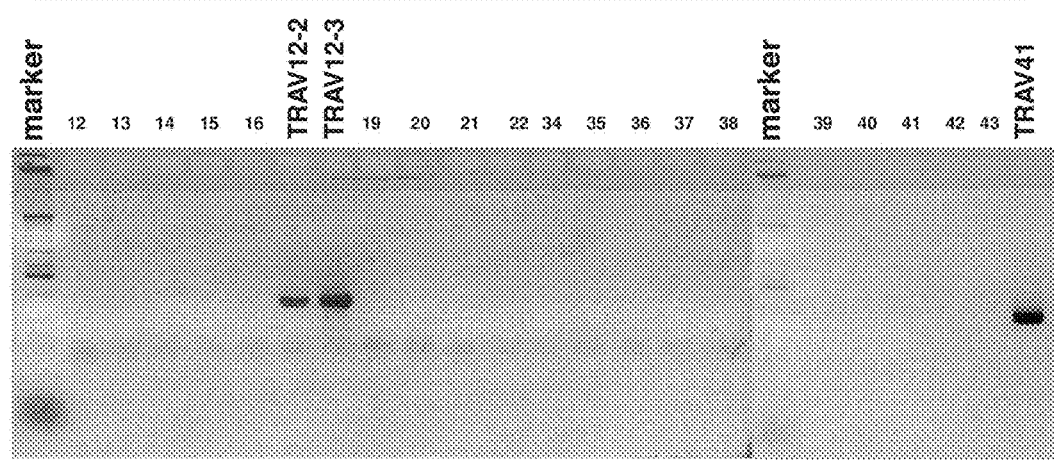
FIG. 5 shows an electrophoresis image (above) for illustrating the result of PCR carried out with a template of a cDNA obtained using a mix of forward primers specific to TCR α-chain and one reverse primer designed for Cα region of TCR α-chain, and an electrophoresis image (below) for illustrating the result of PCR carried out with a template of a cDNA obtained using a forward primer specific to a TRBV5-1 signal sequence registered in IMGT® and two reverse primers (TRBC1 and TRBC2) specific to a TCR Cβ region.
Figure 5:
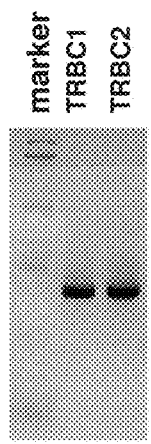

Using RNeasy Protect Mini Kit (QIAGEN GmbH), the total RNA was collected from the cryopreserved cell population described above. Subsequently, cDNAs were prepared using Oligo (dT)$_{20}$ primer according to the manual of SuperScript III First-Strand Synthesis System (Life Technologies Corporation). PCR was carried out with a template of a cDNA obtained using one reverse primer designed for a Cα region of TCR α-chain and four primer mixes comprehensively designed, each of which was a mixture of 10 or 11 forward primers specific to TCR α-chain, in order to obtain the full-length sequence of TCR α-chain. As a result, PCR products were obtained by two of the primer mixes. Using individual forward primers included in the two primer mixes and one reverse primer designed for a Cα region, PCR was carried out using the obtained cDNA as a template. From the result of FIG. 3, the full-length sequence of TCR Vβ of TCR β-chain was TRBV5-1. Hence, PCR was performed with a template of cDNA obtained using a forward primer specific to the TRBV5-1 signal sequence registered in IMGT® and two reverse primers (TRBC1 and TRBC2) specific to a TCR Cβ region. FIG. 5 shows the result of separating the amplified PCR product by electrophoresis on a 1% agarose gel. As to TCR α-chain, PCR products having a full-length sequence were obtained from TRAV12-2, TRA12-3, and TRAV41. Meanwhile, as to TCR β-chain, PCR products were obtained from both of TRBC1 and TRBC2. The PCR products were excised from the agarose gel, and purified using MinElute Gel Extraction Kit (QIAGEN GmbH). After the gene fragments were inserted into pCR2.1-TOPO using TOPO TA Cloning Kit (Life Technologies Corporation), the DNA sequences were analyzed according to the conventional method.

As a result, as to TCR α-chain, the PCR products of TRAV12-2 and TRA12-3 had exactly the same DNA sequence. As to TCR β-chain, the PCR products of TRBC1 and TRBC2 also had the same DNA sequence. Using an IMGT® database, a repertoire analysis was performed on the sequence information thus read. Two types of 37F8-derived TCR α-chain were identified, and the Vα-Jα arrangements were TRAV12-3/TRAJ52/TRAC (hereinafter referred to as "A12-3") and TRAV41/TRAJ47/TRAC (hereinafter referred to as "A41") (see FIG. 14). One type of 37F8-derived TCR β-chain was identified, and the Vβ/Dβ/Jβ/Cβ arrangement was TRBV5-1/TRBD2/TRBJ2-5/TRBC2 (hereinafter referred to as "B5-1") (see FIG. 15).

[Example 5] Expression in Cultured Cell Lines and Checking Combination of TCR α-Chain and β-Chain In order to elucidate a correct combination of the two TCR α-chains (A12-3 and A41) and one β-chain (B5-1) derived from 37F, the cDNAs were subcloned in mammalian cell expression vectors pcDNA3.1 (Invitrogen Corporation) and pEF6/Myc-His (Invitrogen Corporation). As a control, cDNAs of α-chain and β-chain of TCR specific to HLA-A*02:01 Mart-1 were artificially synthesized, and an expression vector was similarly constructed (J. Immunol., 2008; 181: 1063-1070).

Culture cell lines used for the gene introduction were Sup-T1 deficient in TCR α-chain and J.RT3-T3.5 deficient in TCR β-chain, a variant of Jurkat derived from human leukemia. It was confirmed by flow cytometry using an anti-TCR pan α/β antibody (Beckman Coulter, Inc.) that these two cell lines did not express TCR on the cell surface. The genes were introduced by an electroporation method using GENE PULSER® (Bio-Rad Laboratories, Inc.). After static culturing for 3 days, portions of the cell populations were sorted, stained with the HLA-A*24:02 WT1 tetramer reagent, and analyzed with a flow cytometer.

Figure 6:
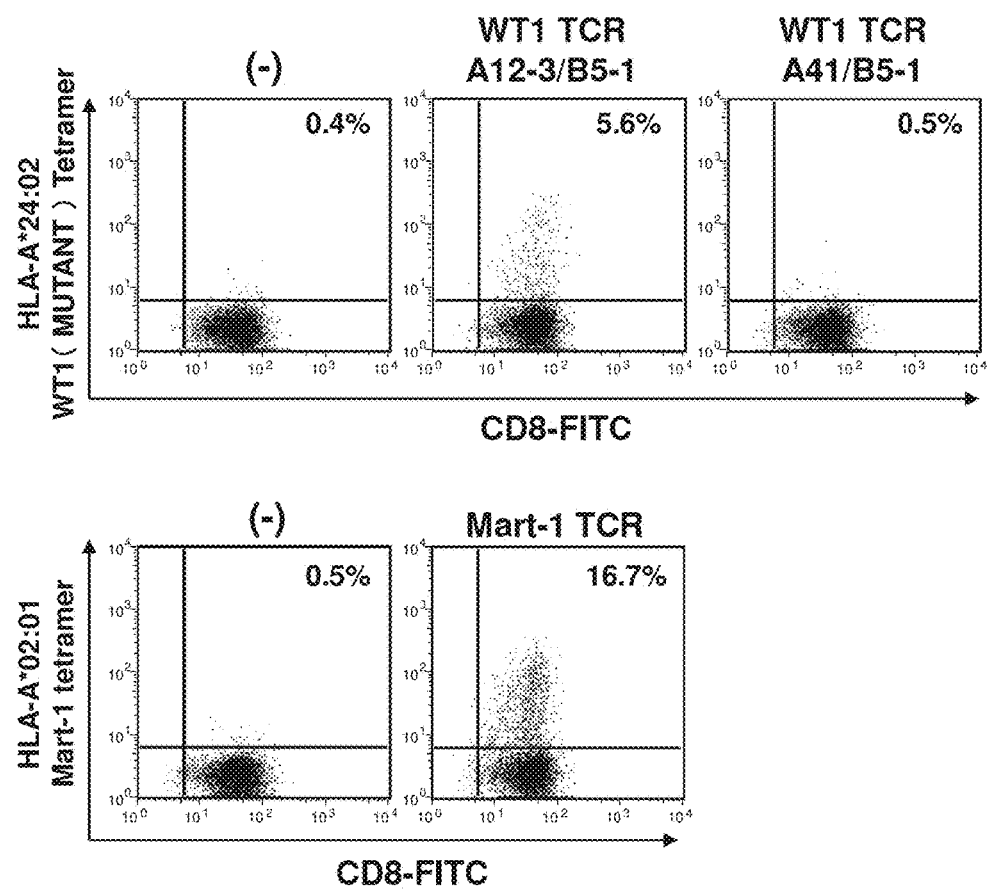
FIG. 6 shows charts for illustrating the result of detecting a reactivity to the HLA-A*24:02 WT1 tetramer reagent of cells expressing a37F8-derived combination of TCR α-chain (A12-3 or A41) and one β-chain (B5-1). As a control, α-chain and β-chain of TCR specific to HLA-A*02:01 Mart-1 were used. The X axis represents the staining intensity (log scale) of the FITC-labeled anti-CD8 antibody, and the Y axis represents the staining intensity (log scale) of the PE-labeled MHC tetramer reagents.

FIG. 6 shows the result. The X axis represents the staining intensity (log scale) of the FITC-labeled anti-CD8 antibody, and the Y axis represents the staining intensity (log scale) of the PE-labeled MHC tetramer reagent. The cell population (−) into which the genes were introduced with pcDNA3.1 and pEF6/Myc-His and the cell population WT1 TCR A41/B5-1 into which the genes were introduced with pcDNA3.1-A41 and pEF6/Myc-His-B5-1 were not verified to be a cell population positive for the HLA-A*24:02 WT1 (mutant) tetramer reagent. On the other hand, 5.6% of the cell population WT1 TCR A12-3/B5-1 into which the genes were introduced with pcDNA3.1-A12-3 and pEF6/Myc-His-B5-1 was verified to be cells positive for the HLA-A*24:02 WT1 (mutant) tetramer reagent. Additionally, 16.7% of the cell population into which the genes of α-chain and β-chain of Mart-1 TCR were similarly introduced as the control was verified to be a cell population positive for a HLA-A*02:01 Mart-1 tetramer reagent.

From the above, it was revealed that 37F8-derived TCR capable of specifically binding to the HLA-A*24:02 WT1 tetramer reagent had TCR α-chain of TRAV12-3/TRAJ52/

Figure 7:
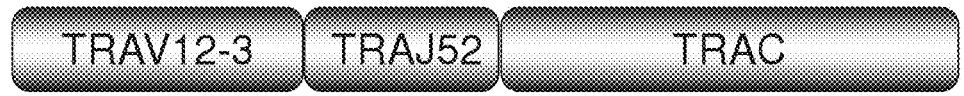
FIG. 7 shows representations for illustrating structures of 37F8-derived TCR α-chain and TCR β-chain capable of specifically binding to the HLA-A*24:02 WT1 tetramer reagent.
Figure 7:
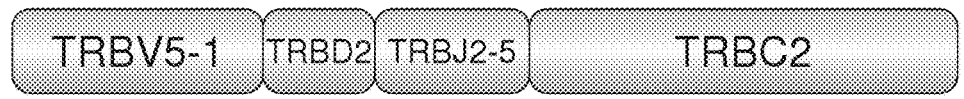

TRAC and TCR β-chain of TRBV5-1/TRBD2/TRBJ2-5/TRBC2. FIG. 7 shows schematic representations of the identified TCR.

[Example 6] Establishment of TCR Gene Expressing Transformed Cells (SK37)

Figure 8:
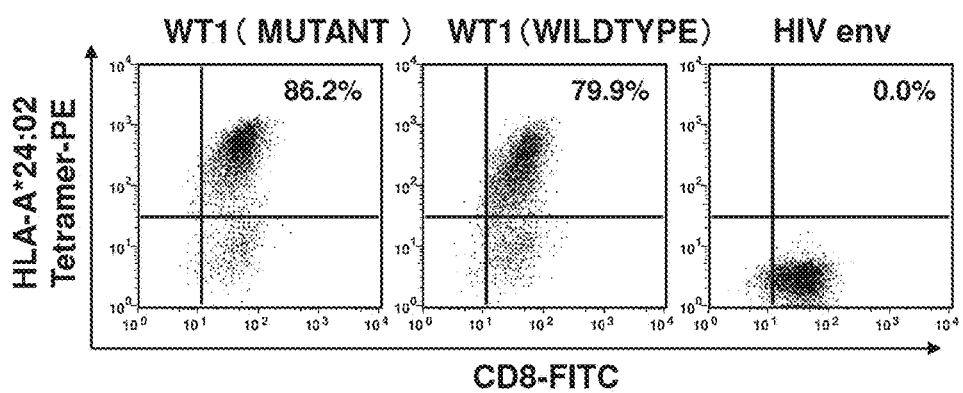
FIG. 8 shows dot plot charts for illustrating the result of detecting a reactivity of a drug-resistant TCR-gene expressing transformed cell line SK37 to the MHC tetramer reagents. The X axis represents the staining intensity (log scale) of the FITC-labeled anti-CD8 antibody, and the Y axis represents the staining intensity (log scale) of the PE-labeled MHC tetramer reagent. The upper portions of the dot plots indicate the type of MHC tetramer reagent used. The upper right quadrant of each dot plot shows an existing ratio (%) of cells positive for the anti-CD8 antibody and positive for the corresponding MHC tetramer reagent in viable cells.

To the cell population WT1 TCR A12-3/B5-1 having produced the positive image, G418 (Roche Diagnostics) and Blastisidin (Invitrogen Corporation) were added, which were drugs each of the vectors capable of resisting to. Thus, a drug-resistant TCR gene expressing transformed cell line SK37 was established. FIG. 8 shows the result of examining a reactivity of SK37 to the MHC tetramer reagents. The X axis represents the staining intensity (log scale) of the FITC-labeled anti-CD8 antibody, and the Y axis represents the staining intensity (log scale) of the PE-labeled MHC tetramer reagents. The upper portions of the dot plots indicate the type of MHC tetramer reagent used. The upper right quadrant of each dot plot shows an existing ratio (%) of cells positive for the anti-CD8 antibody and positive for the corresponding MHC tetramer reagent in viable cells.

SK37 reacted with the HLA-A*24:02 WT1 (mutant) tetramer reagent in 86.2% of the cell population, and the MFI was 459. SK37 reacted with the HLA-A*24:02 WT1 (wildtype) tetramer reagent in 79.9% of the cell population, and the MFI was 282. A ratio of the MFI between the HLA-A*24:02 WT1 (wildtype) tetramer reagent and the HLA-A*24:02 WT1 (mutant) tetramer reagent was approximately 1.6. This result shows that the ratio was slightly lowered in comparison with that of the 37F8 cell population of approximately 2 (Example 1). On the other hand, no specific staining was observed with HLA-A*24:02 HIV env tetramer RYLRDQQLL-PE used as the control of the MHC tetramer reagents. It can be thought from the above that the genetic information on TCR existing in 97% of the 37F8 cell population and binding to HLA-A*24:02 WT1 tetramer reagent was accurately reflected in SK37.

[Example 7] Evaluation of HLA-A*24:02 WT1 Tetramer Reagents Using SK37 (Recovery Test)

In order to check the accuracy of evaluating the HLA-A*24:02 WT1 tetramer reagents using SK37 cells, a recovery test was conducted. The experimental method was as follows. SK37 was mixed with the parental cells having no TCR gene introduced therein, and stained with the HLA-A*24:02 WT1 tetramer reagents. Then, the positive ratio was compared with a positive ratio expected from the mixing ratio. During the culturing, 20 µL of the cell suspension was sorted from SK37 and the parental cell line, to which 20 µL of Trypan Blue Stain 0.4% (Life Technologies Corporation) was added. Then, the number of viable cells was counted with a hemocytometer. SK37 and the parental cell line were mixed to prepare cell populations having a SK37-existing ratio of 100%, 50%, 25%, 15%, 10%, 5%, 2.5%, 1%, and 0%. From each of the cell populations, $5 \times 10^5$ cells were sorted into Eppendorf tubes, and centrifuged at 400×g for 5 minutes. Then, the supernatant was carefully discarded. To the resultant, 1 mL of an FCM buffer was added for resuspension. After centrifugation at 400×g for 5 minutes, the supernatant was carefully discarded. To the resultant, 20 µL of an FCM buffer and 10 µL of Clear Back Human FcR blocking reagent were added and thoroughly stirred. Subsequently, the mixture was allowed to react at room temperature for 5 minutes. After 10 µL of the HLA-A*24:02 WT1 (wildtype) tetramer reagent or the HLA-A*24:02 WT1 (mutant) tetramer reagent was added and gently stirred, the mixture was allowed to react in a cold chamber for 30 minutes. To this, 10 µL of CD8 (clone T8)-FITC was added and allowed to react in the cold chamber for 20 minutes. An appropriate amount of an FCM buffer was added thereto and centrifuged at 400×g for 5 minutes. The supernatant was carefully discarded. To the resultant, 400 µL of an FCM buffer supplemented with 7-AAD by 1% was added to suspend the cells therein. The cells were loaded into a flow cytometer for analysis. A data analysis was performed on a "R1 and R2" cell population, where R1 denotes a region selected in a FCS/SSC dot plot distribution chart, and R2 denotes a viable cell region (i.e., 7-AAD negative cell population) in a FCS/7-AAD dot plot distribution chart.

Figure 9:
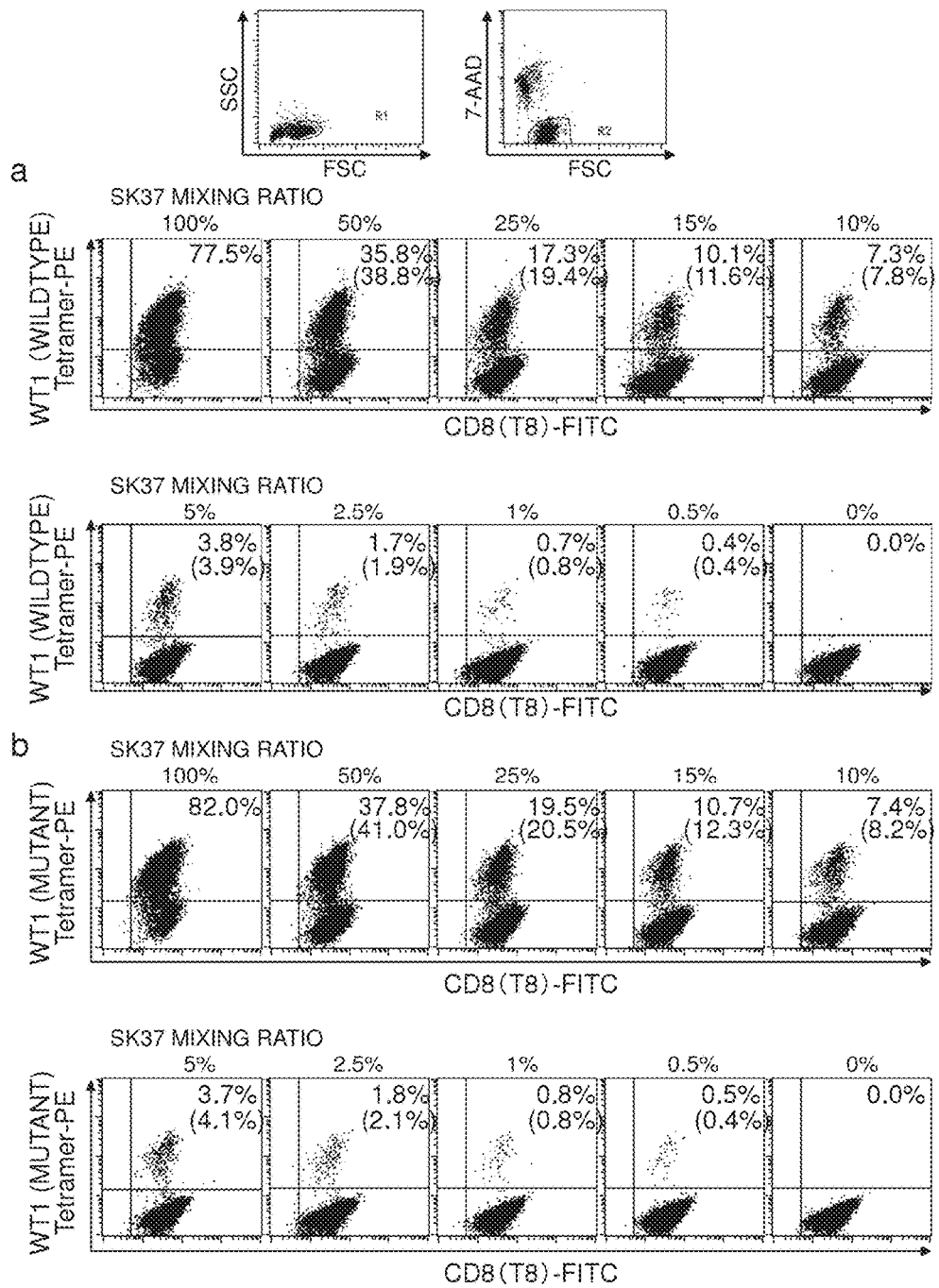
FIG. 9 shows dot plot distribution charts for illustrating the result of a recovery test conducted to evaluate performances of the HLA-A*24:02 WT1 tetramer reagents using SK37. The X axis represents the staining intensity (log scale) of the FITC-labeled anti-CD8 antibody, and the Y axis represents the staining intensity (log scale) of the PE-labeled MHC tetramer reagent. (a) shows the result of staining using the HLA-A*24:02 WT1 (wildtype) tetramer reagent. The upper right quadrant of each dot plot distribution chart shows a positive ratio at a corresponding SK37 mixing ratio. Note that since the positive ratio with SK37 of 100% was 77.5%, a positive expected from the mixing ratio is shown in ratio parentheses in the upper right quadrant of the dot plot distribution chart. (b) shows the result of staining using the HLA-A*24:02 WT1 (mutant) tetramer reagent. Since the positive ratio with SK37 of 100% was 82.0%, a positive ratio expected from the mixing ratio is shown in parentheses in the upper right quadrant of the dot plot distribution chart.

Parts a and b of FIG. 9 show the result. The X axis represents the staining intensity (log scale) of the FITC-labeled anti-CD8 antibody, and the Y axis represents the staining intensity (log scale) of the PE-labeled MHC tetramer reagents. Part a of FIG. 9 shows the result of staining using the HLA-A*24:02 WT1 (wildtype) tetramer reagent. The upper right quadrant of each dot plot distribution chart shows a positive ratio at a corresponding SK37 mixing ratio. Since the positive ratio with SK37 of 100% was 77.5%, a positive ratio expected from the mixing ratio is shown in parentheses in the upper right quadrant of the dot plot distribution chart. Part b of FIG. 9 shows the result of staining using the HLA-A*24:02 WT1 (mutant) tetramer reagent. Since the positive ratio with SK37 of 100% was 82.0%, a positive ratio expected from the mixing ratio is shown in parentheses in the upper right quadrant of the dot plot distribution chart. The result of this recovery test revealed that the mixing ratio of the SK37 cells was accurately detected as the positive ratio using the HLA-A*24:02 WT1 tetramer reagents.

[Example 8] Evaluation of HLA-A*24:02 WT1 Tetramer Reagents Using SK37 (Examination of Concentration Dependent Stain Ability and Checking of Storage Stability)

Positive control cells are essential to check the storage stability of a MHC tetramer reagent used in a flow cytometer. It is important that the positive control cells always exhibit the same reactivity to a reagent. It can be said that stable transformed cells, such as SK37, comprising the genes of the TCR to which HLA-A*24:02 WT1 tetramer reagents bind, are ideal positive control cells. The present inventors examined a method for conducting a storage stability test on the MHC WT1 tetramer reagents using SK37. The storage stability of the MHC tetramer reagents can be evaluated as a period during which a positive ratio desired in flow cytometry is retained. The storage stability was examined by adjusting the positive ratio of SK37 to 5% to 15%, regularly checking the reactivity across a reagent-dilution series, and analyzing ratios of positive ratio and MFI between cells positive for the HLA-A*24:02 WT1 (wildtype) tetramer reagent and cells positive for the HLA-A*24:02 WT1 (mutant) tetramer reagent.

Figure 10A:
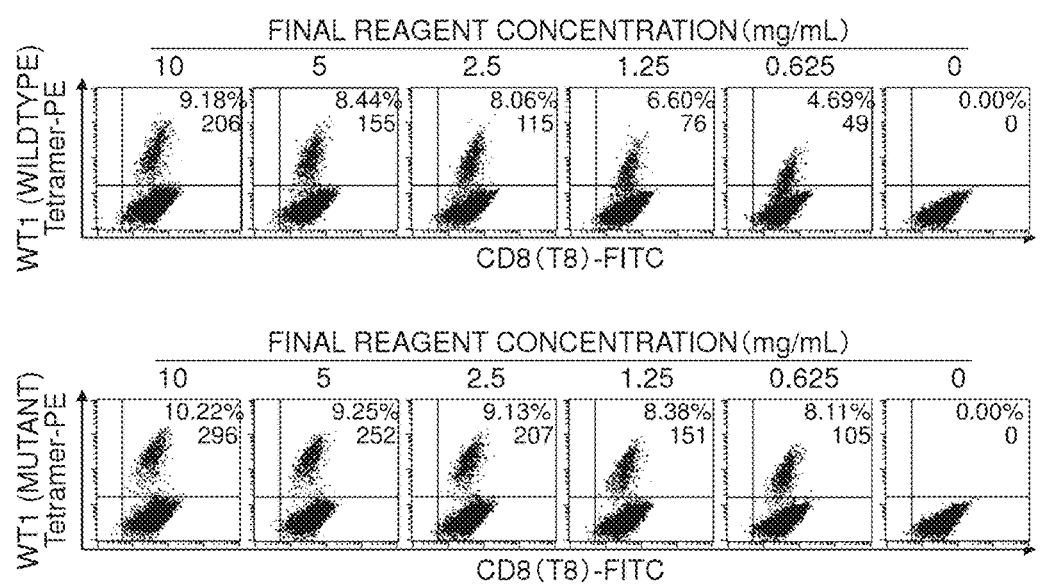
FIG. 10A shows dot plot distribution charts for illustrating the result of evaluating the concentration dependent stain ability of the HLA-A*24:02 WT1 tetramer reagents using SK37. In the charts, the X axis represent the fluorescence intensity (log scale) of the FITC-labeled CD8 antibody, and the Y axis represents the fluorescence intensity (log scale) of the HLA-A*24:02 WT1 tetramer reagents. The upper charts show the result of staining with the HLA-A*24:02 WT1 (wildtype) tetramer reagent, and the lower charts show the result of staining with the HLA-A*24:02 WT1 (mutant) tetramer reagent. The upper right quadrant of each dot plot distribution chart shows a positive ratio and MFI of a cell population positive for the corresponding MHC tetramer reagent and positive for CD8.
Figure 10B:
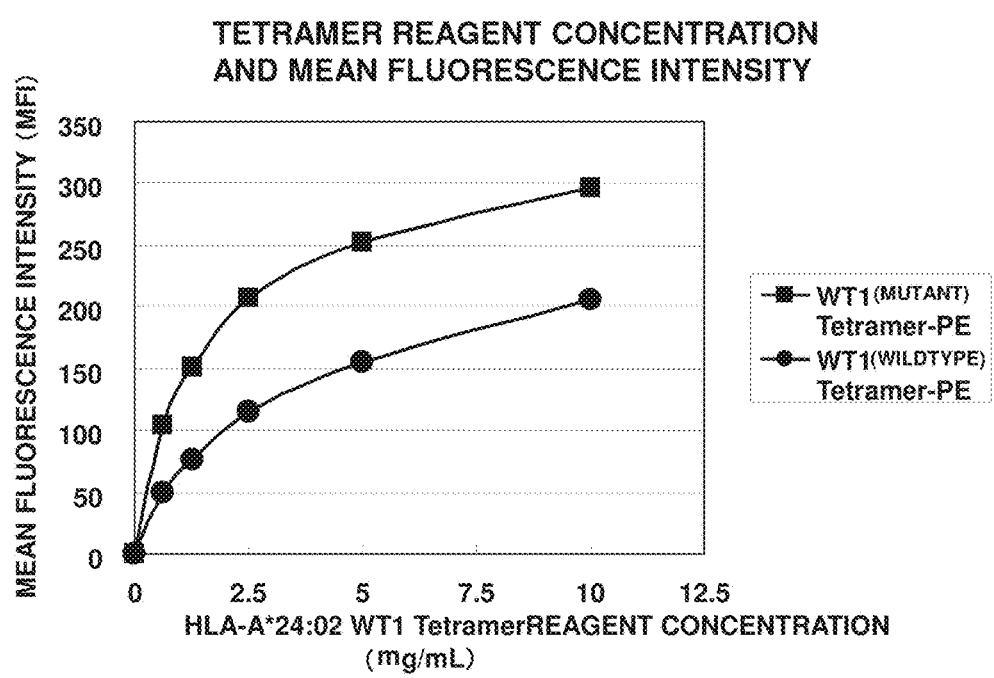
FIG. 10B is a graph for illustrating the result of evaluating the concentration dependent stain ability of the HLA-A*24:02 WT1 tetramer reagents using SK37. The graph shows a relation between the MFI and the reagent concentration.
Figure 10C:
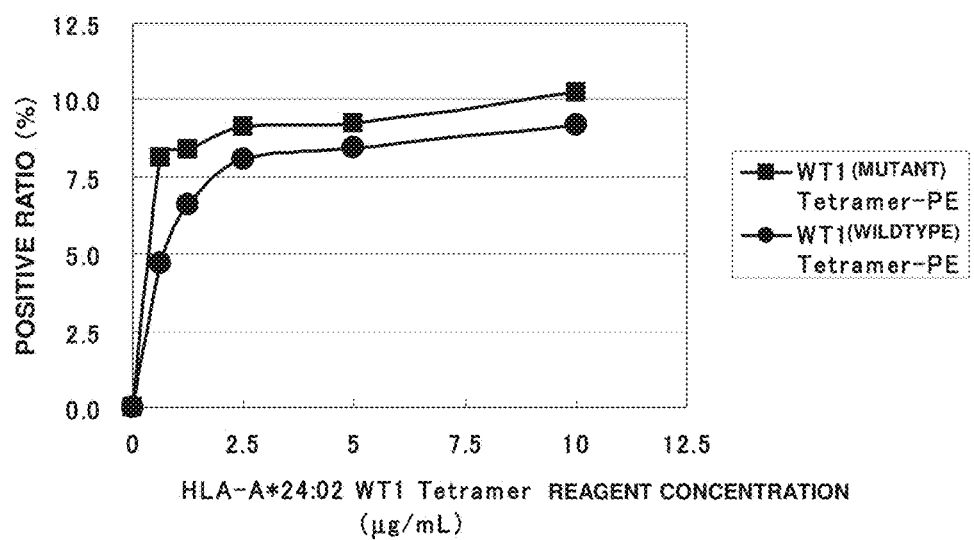
FIG. 10C is a graph for illustrating the result of evaluating the concentration dependent stain ability of the HLA-A*24:02 WT1 tetramer reagents using SK37. The graph shows a relation between the positive ratio and the reagent concentration.

FIG. 10 shows data on a test conducted, as one example of the storage stability test, 49 days after the HLA-A*24:02 WT1 tetramer reagents were produced. The test was conducted using a cell population with an existing ratio of the SK37 cells adjusted to 12.5%. The HLA-A*24:02 WT1 tetramer reagents were adjusted, so that the concentrations in terms of purified biotinylated monomer in a reaction solution were 10, 5, 2.5, 1.25, 0.625, and µg/mL. In FIG. 10A, the X axis represents the fluorescence intensity (log scale) of the FITC-labeled CD8 antibody, and the Y axis represents the fluorescence intensity (log scale) of the HLA-A*24:02 WT1 tetramer reagents. The upper charts show the result of staining with the HLA-A*24:02 WT1 (wildtype) tetramer reagent, and the lower charts shows the result of staining with the HLA-A*24:02 WT1 (mutant) tetramer reagent. The upper right quadrant of each dot plot distribution chart shows a positive ratio and MFI of a cell population positive for the corresponding MHC tetramer reagent and positive for CD8. FIG. 10B shows a graph for illustrating a relation between the MFI and the reagent concentration. FIG. 10C shows a graph for illustrating a relation between the positive ratio and the reagent concentration.

Figure 11A:
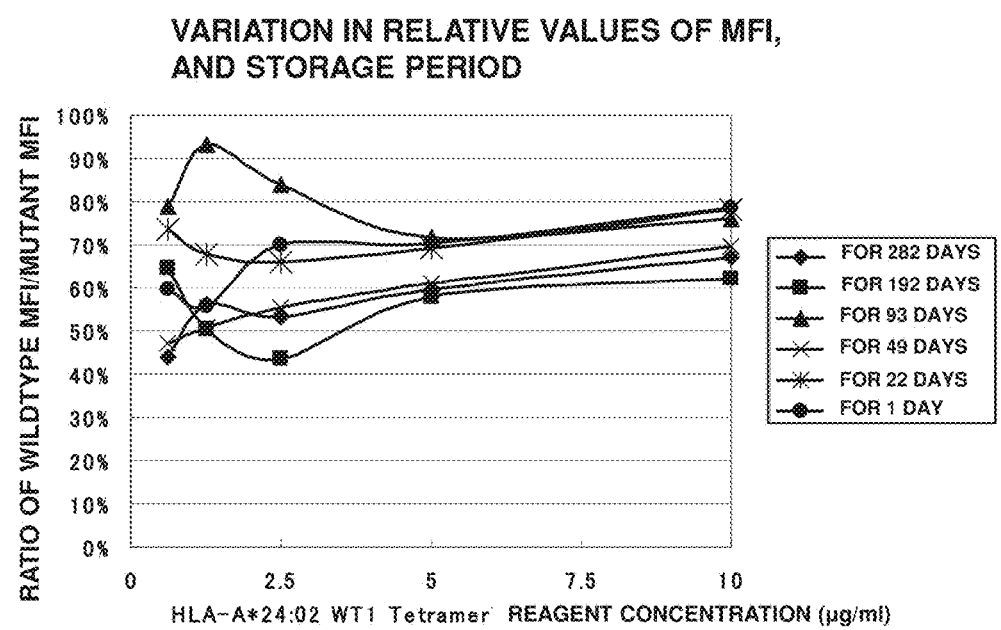
FIG. 11A is a graph for illustrating the result of evaluating a relation between the concentration dependent stain ability and the storage stability of the HLA-A*24:02 WT1 tetramer reagents using SK37. A ratio of the MFI between the HLA-A*24:02 WT1 (wildtype) tetramer reagent and the HLA-A*24:02 WT1 (mutant) tetramer reagent is summarized.
Figure 11B:
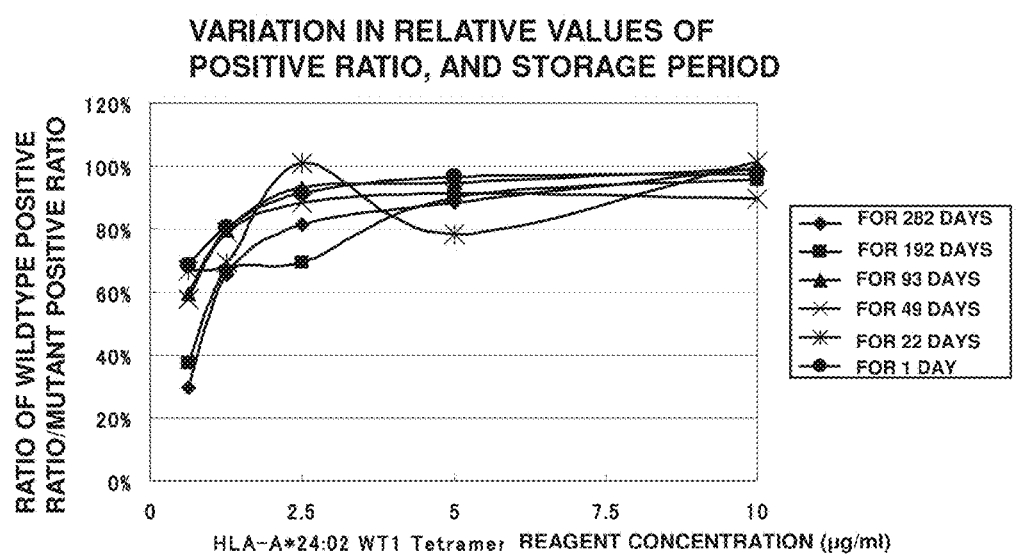
FIG. 11B is a graph for illustrating the result of evaluating a relation between the concentration dependent stain ability and the storage stability of HLA-A*24:02 WT1 tetramer reagents using SK37. A ratio of the positive ratio between the HLA-A*24:02 WT1 (wildtype) tetramer reagent and the HLA-A*24:02 WT1 (mutant) tetramer reagent is summarized.

These results revealed that the MFI with the HLA-A*24:02 WT1 (wildtype) tetramer reagent was approximately ¼ of that with the HLA-A*24:02 WT1 (mutant) tetramer reagent. To put it differently, the MFI with the HLA-A*24:02 WT1 (wildtype) tetramer reagent used at 10 µg/mL was substantially equivalent to the MFI with the HLA-A*24:02 WT1 (mutant) tetramer reagent used at 2.5 µg/mL. Interestingly, this ratio is substantially the same as the ratio between the cytotoxic activity (at maximum 73%) on the LCL pulsed with the WT1 (mutant) peptide and the cytotoxic activity (at maximum 20%) on the LCL pulsed with the WT1 (wildtype) peptide (see FIG. 2). FIG. 11A shows a graph summarizing a ratio of the MFI between the HLA-A*24:02 WT1 (wildtype) tetramer reagent and the HLA-A*24:02 WT1 (mutant) tetramer reagent, the ratio obtained by repeating such measurement over time. It is shown that the MFI ratio greatly varied with the final reagent concentration below 5 µg/mL, and accurate staining data is not obtained. Moreover, the graph in FIG. 11B summarizing a ratio of the positive ratio between the HLA-A*24:02 WT1 (wildtype) tetramer reagent and the HLA-A*24:02 WT1 (mutant) tetramer reagent also similarly suggests that accurate staining data is not obtained with the final reagent concentration below 5 µg/mL. In this way, SK37 is useful also for checking the reactivity over time and setting the effective period and recommended dose of a reagent.

[Example 9] Evaluation of HLA-A*24:02 WT1 (Wildtype) Tetramer Reagent Using SK37

Since the WT1 (wildtype) peptide used by the HLA-A*24:02 WT1 (wildtype) tetramer reagent weakly binds to HLA, a precipitate is observed within 2 days after the production of the reagent. When the MHC tetramer reagent is analyzed by HPLC, the instability can also be grasped from a decrease in a peak area indicating an active ingredient of the reagent. Nevertheless, the association between the HPLC analysis data and the stain ability data obtained using a flow cytometer has been unknown for a long time because no positive control cells have existed. For this reason, developed was a kit, which is prepared at the time of use and adjustable immediately before the HLA-A*24:02 WT1 (wildtype) tetramer reagent is used, and a change in reactivity over time was examined using SK37 after the reagent was prepared for use and refrigerated at 2 to 8° C. for storage.

Figure 12:
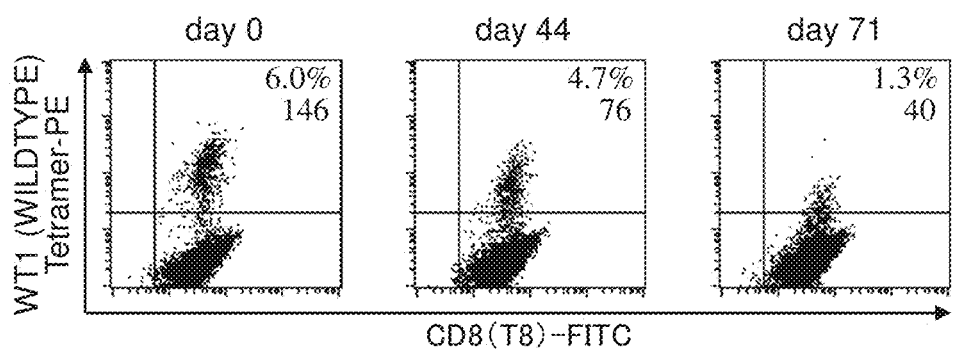
FIG. 12 shows dot plot distribution charts for illustrating the result of evaluating, using SK37, an influence of time on the reactivity of the HLA-A*24:02 WT1 (wildtype) tetramer reagent after the reagent was prepared at the time of use. The X axis represents the fluorescence intensity (log scale) of the FITC-labeled CD8 antibody, and the Y axis represents the fluorescence intensity (log scale) of the HLA-A*24:02 WT1 tetramer reagent. The upper portions of the charts indicate days during which the HLA-A*24:02 WT1 (wildtype) tetramer reagent prepared at the time of use was stored in a cold chamber. The upper right quadrant of each dot plot distribution chart shows a positive ratio and MFI of a cell population positive for the corresponding MHC tetramer reagent and positive for CD8.

FIG. 12 shows the result. The X axis represents the fluorescence intensity (log scale) of the FITC-labeled CD8 antibody, and the Y axis represents the fluorescence intensity (log scale) of the HLA-A*24:02 WT1 tetramer reagent. The upper portions of dot plot distribution charts indicate days during which the HLA-A*24:02 WT1 (wildtype) tetramer reagent prepared at the time of use was stored in a cold chamber. The upper right quadrant of each dot plot distribution chart shows a positive ratio and MFI of a cell population positive for the MHC tetramer reagent and positive for CD8.

It was revealed that the reactivity of the HLA-A*24:02 WT1 (wildtype) tetramer reagent on day 44 and day 71 after prepared and left standing in the cold chamber for storage was significantly lowered in comparison with that immediately after the reagent was prepared using the kit prepared at the time of use (day 0).

Note that all the data on the HLA-A*24:02 WT1 (wildtype) tetramer reagent used in Examples other than the present Example were obtained within 24 hours after the preparation for use.

[Example 10] Detection of Antigen-Presenting Cells Using TCR A-Chain and B-Chain Using a cell line (hereinafter referred to as "JSK37"), which was the Jurkat cell subline described in Example 5, and which stably expressed TCR specific to HLA-A*24:02 WT1, the present Example examined whether it was possible to inspect a target peptide presented by HLA on the cell surface on the basis of IL-2 production by the cells. Incidentally, it has been reported so far that Jurkat cells produce IL-2 by stimuli of anti-CD3 antibody and PMA (J. Immunology, 1984; 133: 1123-1128).

HLA-A*24:02 positive LCL was pulsed with the WT1 (wildtype) peptide or the WT1 (mutant) peptide, and the number of cells was counted. $1 \times 10^5$ of the JSK37 cells and $16 \times 10^4$ of LCL not pulsed with the peptide or $0.125 \times 10^4$, $0.5 \times 10^4$, $2 \times 10^4$, $8 \times 10^4$, or $16 \times 10^4$ of the LCL pulsed with the peptide were prepared, and then mixed and cultured in 200 µL of a medium in a U-bottomed 96-well plate. The culturing was continued for 24 hours in a 5% $CO_2$ incubator at 37° C. After the culturing and centrifugation at 400×g for 5 minutes, 150 µL of the supernatant was taken from the U-bottomed 96-well plate to measure the IL-2 concentration using Human IL-2 Quantikine ELISA Kit (R&D Systems, Inc.).

Figure 13:
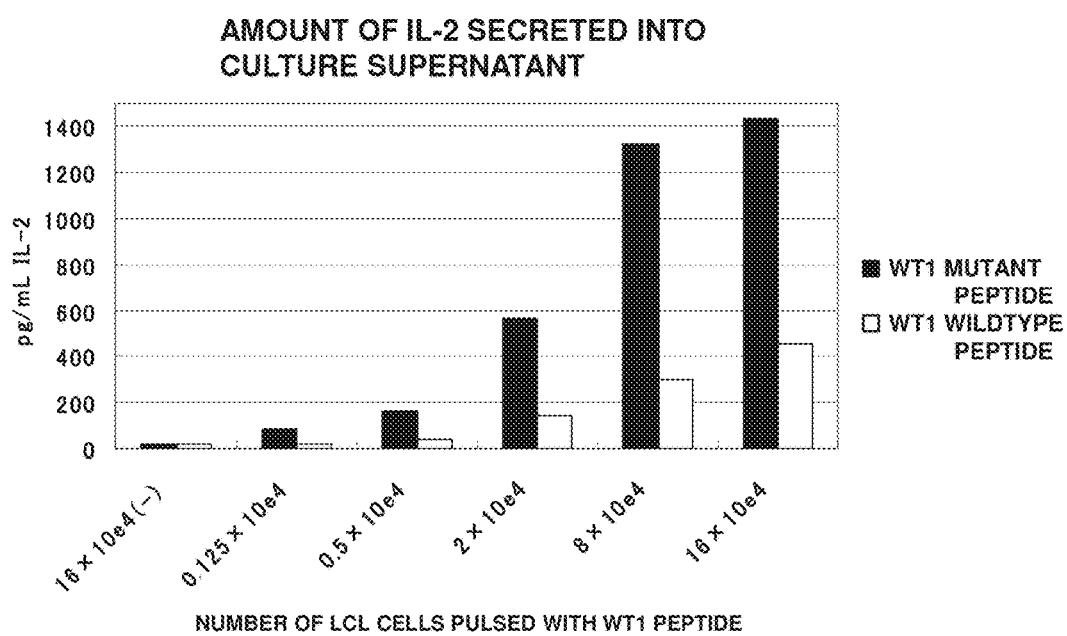
FIG. 13 is a graph for illustrating the result of detecting antigen-presenting cells using a cell line expressing α-chain and β-chain of TCR specific to HLA-A*24:02 WT1. The graph shows a relation between the concentration of IL-2 secreted from the cell line and the number of LCL cells. The X axis represents the number of LCL cells, and the Y axis represents the concentration of IL-2 secreted into the culture supernatant.

FIG. 13 shows the result. The X axis represents the number of the LCL cells, and the Y axis represents the concentration of IL-2 secreted into the culture supernatant. It was revealed that JSK37 recognized the LCL pulsed with the WT1 peptide and produced IL-2 in a manner dependent on the cell count. This means that when the same experiment is conducted using a biopsy sample from a patient, it is possible to determine whether the WT1 peptide is presented by HLA-A*24:02 on the cell membrane surface of a cell population contained in the biopsy sample.

The TCR provided according to the present invention is capable of recognizing both a state where a wildtype WT1 specific peptide is presented by HLA-A*24:02 and a state where a mutant WT1 specific peptide is presented by HLA-A*24:02. Cells expressing the TCR of the present invention and molecules multimerized with the TCR of the present invention are usable as a companion diagnostic agent in performing a peptide vaccination, or as a reagent for checking whether or not a target peptide is presented by an HLA on dendritic cells when a dendritic cell vaccination is performed. Moreover, such cells and molecules can also be utilized as a tool for delivering a drug to cancer cells, and further utilized for quality management of WT1 tetramer reagents. Therefore, the present invention can greatly contribute mainly to the medical field and related research fields.

What is claimed is:

1. A nucleic acid comprising: (1) a cDNA sequence encoding a T cell receptor α-chain protein having the amino acid sequences of SEQ ID NOs: 1 to 3; and (2) a cDNA sequence encoding a T cell receptor β-chain protein having the amino acid sequences of SEQ ID NOs: 5 to 7.

2. A cDNA encoding a T cell receptor β-chain protein having the amino acid sequences of SEQ ID NOs: 5 to 7.

3. A vector comprising (a) or (b) below:
   (a) a DNA encoding a T cell receptor α-chain protein having the amino acid sequences of SEQ ID NOs: 1 to 3, and a DNA encoding a T cell receptor β-chain protein having the amino acid sequences of SEQ ID NOs: 5 to 7; or
   (b) a DNA encoding a T cell receptor β-chain protein having the amino acid sequences of SEQ ID NOs: 5 to 7.

4. A transformed cell comprising (a) or (b) below:
   (a) a DNA encoding a T cell receptor α-chain protein having the amino acid sequences of SEQ ID NOs: 1 to 3, and a DNA encoding a T cell receptor β-chain protein having the amino acid sequences of SEQ ID NOs: 5 to 7; or
   (b) a DNA encoding a T cell receptor β-chain protein having the amino acid sequences of SEQ ID NOs: 5 to 7.

5. A transformed cell comprising a DNA encoding a T cell receptor α-chain protein having the amino acid sequences of SEQ ID NOs: 1 to 3 and a DNA encoding a T cell receptor β-chain protein having the amino acid sequences of SEQ ID NOs: 5 to 7, the transformed cell being detectable by a molecule multimerized by binding a wildtype WT1 peptide restricted to HLA-A*24:02 and a molecule multimerized by binding a mutant WT1 peptide restricted to HLA-A*24:02.

6. The transformed cell according to claim 4, which is a lymphocyte.

7. A pharmaceutical composition for treating a WT1 positive cancer, the pharmaceutical composition comprising the transformed cell according to claim 6 as an active ingredient.

8. A kit for detecting any one of a wildtype WT1 peptide restricted to HLA-A*24:02 and a mutant WT1 peptide restricted to HLA-A*24:02, the kit comprising at least one of (d) to (f) below and instructions for using the kit:
   (d) a cDNA encoding a T cell receptor α-chain protein having the amino acid sequences of SEQ ID NOs: 1 to 3, and a cDNA encoding a T cell receptor β-chain protein having the amino acid sequences of SEQ ID NOs: 5 to 7;
   (e) a vector comprising a DNA encoding a T cell receptor α-chain protein having the amino acid sequences of SEQ ID NOs: 1 to 3, and a DNA encoding a T cell receptor β-chain protein having the amino acid sequences of SEQ ID NOs: 5 to 7; or
   (f) a transformed cell comprising a DNA encoding a T cell receptor α-chain protein having the amino acid sequences of SEQ ID NOs: 1 to 3, and a DNA encoding a T cell receptor β-chain protein having the amino acid sequences of SEQ ID NOs: 5 to 7; or
   (f)(2) a transformed cell comprising a DNA encoding a T cell receptor α-chain protein having the amino acid sequences of SEQ ID NOs: 1 to 3 and a DNA encoding a T cell receptor β-chain protein having the amino acid sequences of SEQ ID NOs: 5 to 7, the transformed cell being detectable by a molecule multimerized by binding a wildtype WT1 peptide restricted to HLA-A*24:02 and a molecule multimerized by binding a mutant WT1 peptide restricted to HLA-A*24:02; and
   (f)(3) the transformed cell according to (f)(1), which is a lymphocyte.

9. A nucleic acid comprising: (1) a cDNA sequence encoding a T cell receptor α-chain protein having the amino acid sequence of SEQ ID NO: 4; and (2) a cDNA sequence encoding a T cell receptor β-chain protein having the amino acid sequence of SEQ ID NO: 8.

10. A nucleic acid comprising: (1) a cDNA sequence encoding a T cell receptor α-chain protein having the amino acid sequence of SEQ ID NO: 14; and (2) a cDNA sequence encoding a T cell receptor β-chain protein having the amino acid sequence of SEQ ID NO: 15.

11. A cDNA encoding a T cell receptor β-chain protein having the amino acid sequence of SEQ ID NO: 8.

12. A cDNA encoding a T cell receptor β-chain protein having the amino acid sequence of SEQ ID NO: 15.

13. A vector comprising one of (a) to (d) below:
   (a) a DNA encoding a T cell receptor α-chain protein having the amino acid sequence of SEQ ID NO: 4, and a DNA encoding a T cell receptor β-chain protein having the amino acid sequence of SEQ ID NO: 8;
   (b) a DNA encoding a T cell receptor α-chain protein having the amino acid sequence of SEQ ID NO: 14, and a DNA encoding a T cell receptor β-chain protein having the amino acid sequence of SEQ ID NO: 15;
   (c) a DNA encoding a T cell receptor β-chain protein having the amino acid sequence of SEQ ID NO: 8; or
   (d) a DNA encoding a T cell receptor β-chain protein having the amino acid sequence of SEQ ID NO: 15.

14. A transformed cell comprising one of (a) to (d) below:
   (a) a DNA encoding a T cell receptor α-chain protein having the amino acid sequence of SEQ ID NO: 4, and a DNA encoding a T cell receptor β-chain protein having the amino acid sequence of SEQ ID NO: 8;
   (b) a DNA encoding a T cell receptor α-chain protein having the amino acid sequence of SEQ ID NO: 14, and a DNA encoding a T cell receptor β-chain protein having the amino acid sequence of SEQ ID NO: 15;
   (c) a DNA encoding a T cell receptor β-chain protein having the amino acid sequence of SEQ ID NO: 8; or
   (d) a DNA encoding a T cell receptor β-chain protein having the amino acid sequence of SEQ ID NO: 15.

15. A transformed cell comprising a DNA encoding a T cell receptor α-chain protein having any one of the amino acid sequences of SEQ ID NOs: 4 and 14, and a DNA encoding a T cell receptor β-chain protein having any one of the amino acid sequences of SEQ ID NOs: 8 and 15, the transformed cell being detectable by a molecule multimerized by binding a wildtype WT1 peptide restricted to HLA-A*24:02 and a molecule multimerized by binding a mutant WT1 peptide restricted to HLA-A*24:02.

16. The transformed cell according to claim 15, which is a lymphocyte.

17. A pharmaceutical composition for treating a WT1 positive cancer, the pharmaceutical composition comprising the transformed cell according to claim 15 as an active ingredient.

18. A kit for detecting any one of a wildtype WT1 peptide restricted to HLA-A*24:02 and a mutant WT1 peptide restricted to HLA-A*24:02, the kit comprising at least one of (a) to (c) below and instructions for using the kit:
   (a) a cDNA encoding a T cell receptor α-chain protein having any one of the amino acid sequences of SEQ ID NOs: 4 and 14, and a cDNA encoding a T cell receptor β-chain protein having any one of the amino acid sequences of SEQ ID NOs: 8 and 15;
(b) a vector comprising a DNA encoding a T cell receptor α-chain protein having any one of the amino acid sequences of SEQ ID NOs: 4 and 14, and a DNA encoding a T cell receptor β-chain protein having any one of the amino acid sequences of SEQ ID NOs: 8 and 15; or
(c)(1) a transformed cell comprising a DNA encoding a T cell receptor α-chain protein having any one of the amino acid sequences of SEQ ID NOs: 4 and 14, and a DNA encoding a T cell receptor β-chain protein having any one of the amino acid sequences of SEQ ID NOs: 8 and 15; or
(c)(2) a transformed cell comprising a DNA encoding a T cell receptor α-chain protein having any one of the amino acid sequences of SEQ ID NOs: 4 and 14 and a DNA encoding a T cell receptor β-chain protein having any one of the amino acid sequences of SEQ ID NOs: 8 and 15, the transformed cell being detectable by a molecule multimerized by binding a wildtype WT1 peptide restricted to HLA-A*24:02 and a molecule multimerized by binding a mutant WT1 peptide restricted to HLA-A*24:02; and
(c)(3) the transformed cell according to (c)(1), which is a lymphocyte.

* * * * *